United States Patent
Rosenthal et al.

(10) Patent No.: US 10,227,398 B2
(45) Date of Patent: *Mar. 12, 2019

(54) ANTI-COMPLEMENT FACTOR C1Q ANTIBODIES AND USES THEREOF

(71) Applicant: Annexon, Inc., South San Francisco, CA (US)

(72) Inventors: Arnon Rosenthal, Woodside, CA (US); Michael Leviten, Emerald Hills, CA (US)

(73) Assignee: Annexon, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,574

(22) Filed: Apr. 19, 2017

(65) Prior Publication Data

US 2017/0334976 A1  Nov. 23, 2017

Related U.S. Application Data

(63) Continuation of application No. 14/989,038, filed on Jan. 6, 2016, now Pat. No. 9,708,394, which is a (Continued)

(51) Int. Cl.
*C07K 16/40* (2006.01)
*A61P 25/28* (2006.01)
(Continued)

(52) U.S. Cl.
CPC .......... *C07K 16/18* (2013.01); *A61K 49/0004* (2013.01); *G01N 33/56966* (2013.01); *A61K 2039/505* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/734* (2013.01); *C07K 2317/76* (2013.01); *C07K 2317/92* (2013.01); *G01N 2333/4716* (2013.01)

(58) Field of Classification Search
None
See application file for complete search history.

(56) References Cited

U.S. PATENT DOCUMENTS 6,197,930 B1  3/2001  Sheppard et al.
8,025,878 B2  9/2011  Gellerfors et al.
(Continued)

FOREIGN PATENT DOCUMENTS

EP  1774972 A1  4/2007
EP  2266606 A1  12/2010
(Continued)

OTHER PUBLICATIONS

"Complement C1s antibody (49)," Product Data Sheet. ThermScientific. Pierce Antibody Products. 1995. pp. 1-2. Retrieved from the Internet: <http://www.pierce-antibodies.com/ <http://www.pierce-antibodies.com/> Complement-C1s-antibody-clone-49-monoclonal-ABS0024902.html#> on Sep. 23, 2014 (Sep. 23, 2014).
(Continued)

*Primary Examiner* — Jeffrey Stucker
*Assistant Examiner* — Aurora M Fontainhas
(74) *Attorney, Agent, or Firm* — Foley & Hoag LLP

(57) ABSTRACT

The present invention provides anti-C1q antibodies and methods of using the same.

30 Claims, 7 Drawing Sheets

Specification includes a Sequence Listing.

Related U.S. Application Data continuation of application No. PCT/US2014/046042, filed on Jul. 9, 2014.

(60) Provisional application No. 61/871,813, filed on Aug. 29, 2013, provisional application No. 61/844,369, filed on Jul. 9, 2013.

(51) Int. Cl.
| | |
|---|---|
| *G01N 33/569* | (2006.01) |
| *A61K 49/00* | (2006.01) |
| *C07K 16/18* | (2006.01) |
| *A61K 39/00* | (2006.01) |

(56) References Cited

U.S. PATENT DOCUMENTS

| | | |
|---|---|---|
| 9,708,394 B2 | 7/2017 | Rosenthal et al. |
| 2002/0058311 A1 | 5/2002 | Browne et al. |
| 2002/0066117 A1 | 5/2002 | Nilsson et al. |
| 2002/0104104 A1 | 8/2002 | Games et al. |
| 2002/0160433 A1 | 10/2002 | Welch et al. |
| 2003/0170781 A1 | 9/2003 | Holloway et al. |
| 2004/0248156 A1 | 12/2004 | Hu et al. |
| 2005/0197285 A1 | 9/2005 | Rosen et al. |
| 2005/0214786 A1 | 9/2005 | Birse et al. |
| 2005/0241008 A1 | 10/2005 | Bredesen et al. |
| 2007/0135753 A1 | 6/2007 | Barres et al. |
| 2007/0269435 A1 | 11/2007 | Gillies et al. |
| 2008/0241145 A1 | 10/2008 | Goldenberg et al. |
| 2010/0143343 A1 | 6/2010 | Halstead et al. |
| 2011/0104156 A1 | 5/2011 | Christadoss et al. |
| 2012/0328601 A1 | 12/2012 | Barres et al. |
| 2013/0344073 A1 | 12/2013 | Schwaeble et al. |
| 2014/0140933 A1 | 5/2014 | Van Vlasselaer et al. |
| 2015/0259437 A1 | 9/2015 | Van Vlasselaer et al. |
| 2016/0159890 A1 | 6/2016 | Rosenthal et al. |
| 2016/0326237 A1 | 11/2016 | Rosenthal et al. |
| 2016/0355574 A1 | 12/2016 | Rosenthal et al. |
| 2016/0368973 A1 | 12/2016 | Rosenthal et al. |
| 2017/0152309 A1 | 6/2017 | Yednock et al. |
| 2017/0334976 A1 | 11/2017 | Rosenthal et al. |

FOREIGN PATENT DOCUMENTS

| | | |
|---|---|---|
| WO | WO-85/02261 A1 | 5/1985 |
| WO | WO-1998/23761 A1 | 6/1998 |
| WO | WO-2003/052377 A2 | 6/2003 |
| WO | WO-2005/002513 A2 | 1/2005 |
| WO | WO-2007070375 A2 | 6/2007 |
| WO | WO-2012/067267 A1 | 5/2012 |
| WO | WO-2012/176765 A1 | 12/2012 |
| WO | WO-14066744 A2 | 5/2014 |
| WO | WO-2014/161570 A1 | 10/2014 |
| WO | WO-2014/169076 A1 | 10/2014 |
| WO | WO-14186599 A2 | 11/2014 |
| WO | WO-14186622 A2 | 11/2014 |
| WO | WO-2015/006507 A1 | 1/2015 |
| WO | WO-15006504 A1 | 1/2015 |
| WO | WO-2016/073685 A1 | 5/2016 |
| WO | WO-2017/091719 A1 | 6/2017 |

OTHER PUBLICATIONS

Angal et al., "A Single Amino Acid Substitution Abolishes the Heterogeneity of Chimeric Mouse/Human (IgG4) Antibody," Molecular Immunol, 30(1): 105-108 (1993).
Carroll et al., "Antibody-mediates inhibition of human C1s and the classical complement pathway," Immunobiology, 218:1041-8 (2013).
Hampel et al., "The future of Alzheimer's disease: the next 10 years," Prog Neurobiol, 95(4): 718-28 (Dec. 2011).
Hu et al., "Characterization of C1q in teleosts: insight into the molecular and functional evolution of C1q family and classical pathway," J Biol Chem, 285:28777-28786 (2010).
International Search Report and Written Opinion dated Apr. 2, 2015 from related PCT Application PCT/US14/038239.
International Search Report and Written Opinion dated Mar. 18, 2008 from related PCT Application PCT/US06/046857.
International Search Report and Written Opinion dated Nov. 7, 2014 from related PCT Application PCT/US14/038267.
International Search Report and Written Opinion dated Sep. 3, 2014 from related PCT Application PCT/US14/33560.
International Search Report and Written Opinion for related PCT Application PCT/US2015/059185, dated Jan. 27, 2016.
International Search Report and Written Opinion from corresponding PCT Application PCT/US14/046042, dated Dec. 5, 2014.
International Search Report and Written Opinion from related PCT Application PCT/US14/046045, dated Nov. 4, 2014.
Lopez-Requena et al., "Immunogenicity of autologous immunoglobulins: Principles and practices," Molecular Immunol, 44:3076-82 (2007).
McGonigal, et al., "C1q-targeted inhibition of the classical complement pathway prevents injury in a novel mouse model of acute motor axonal neuropathy," Acta Neuropathologica Comm, 9(3): 729 (2016).
McGreer et al., "The future use of complement inhibitors for the treatment of neurological diseases," Drugs, 55(6):739-46 (1998).
Morgan et al., "The role of complement disorders of the nervous system," Immunopharmacology, 38:43-50 (1997).
Pardridge et al., "Reengineering Biopharmaceuticals for Targeted Delivery Across the Blood-Brain Barrier," Methods in Enzymology, Academic Press, US, 503: 269-292 (Jan. 1, 2012).
Perrin et al., "Multimodal Techniques for Diagnosis and Prognosis of Alzheimer's disease," Nature, 461(7266): 916-922 (Oct. 15, 2009).
Phuan et al., "C1q-targeted monoclonal antibody prevents complement dependent cytotoxicity and neuropathology in in vitro and mouse models of neuromyelitis optica," Acta Neuropathol, 125(6):829-40 (2013).
Reddy et al., "Elimination of Fc Receptor-Dependent Effector Functions of a Modified IgG4 Monoclonal Antibody to Human CD4," J Immunol, 164(4): 1925-1933 (2000).
Roos et al., "Specific inhibition of the classical complement pathway by C1q-binding peptides," J Immunol, 167(12):7052-9 (2001).
Sahu et al., "Complement inhibitors: a resurgent concept in anti-inflammatory therapeutics," Immunopharmacology, 49(1-2):133-48 (2000).
Supplementary European Search Report for European Application No. EP 14 82 2330 dated Nov. 15, 2016.
Tradtrantip et al., "Enzymatic deglycosylation converts pathogenic neuromyelitis optica anti-aquaporin-4 IgG into therapeutic antibody," Ann Neutol, 73(1):77-85 (2013).
Tuzun et al., "Targeting Classical Complement Pathway to Treat Complement Mediated Autoimmune Diseases," Current Topcis in Complement II, Springer US, Jul. 26, 2008. p. 254-261 [online].
Vickers, "A vaccine against Alzheimer's disease: developments to date," Drugs Aging, 19(7): 487-494 (2002).
Brown et al., "Tolerance of single, but not multiple, amino acid replacements in antibody VH CDR 2: a means of minimizing B cell wastage from somatic hypermutation?" J Immunol, 156(9):3285-3291 (1996).
Chen et al., "Enhancement and Destruction of Antibody Function by Somatic Mutation: Unequal Occurrence is Controlled by V Gene Combinatorial Associations," EMBO J, 14: 2784-2794 (1995).
Colman, "Effects of Amino Acid Sequence Changes on Antibody-Antigen Interactions," Research in Immunology, 145: 33-36 (1994).
Extended European Search Report issued by the European Patent Office in corresponding Application No. EP 15857258.6, dated Mar. 20, 2018.
Gershoni et al., "Epitope mapping: the first step in developing epitope-based vaccines," BioDrugs, 21(3):145-156 (2007).
Hoekzema et al., "The Distortive Mechanism for the Activation of Complement Component C1 Supported by Studies with a Monoclonal Antibody against the "arms" of C1q," Mol Immunol, 25(5):485-494 (1988).

(56) References Cited

OTHER PUBLICATIONS

Hsiung et al., "A Monoclonal Antibody to C1q which Appears to Interact with C1r2C1s2-binding site," FEBS Letters, 229(1):21-24 (1988).

International Search Report and Written Opinion for International Application No. PCT/US2016/063587 dated Mar. 9, 2017.

Kilchherr et al., "Activation of the First Component of Human Complement, C1, by Monoclonal Antibodies Directed Against Different omains of Subcomponent C1q," J Immunol, 137(1): 255-262 (1986).

Kussie et al., "A Single Engineered Amino Acid Substitution Changes Antibody Fine Specificity," J Immunol, 152: 146-152 (1994).

Rader, "Overview on Concepts and Applications of Fab Antibody Fragments," Current Protocols in Protein Science, 6.9. 1-6.9. 14 (2009).

Rudikoff et al., "Single Amino Acid Substitution Altering Antigen-Binding Specificity," Proc Natl Acad Sci USA, 79: 1979-1983 (1982).

Tsumura et al., "Feasbility Study of the Fab Fragment of a Monoclonal Antibody Against Tissue Factor as a Diagnostic Tool," Int J Oncol, 47(6): 2107-2114 (2015).

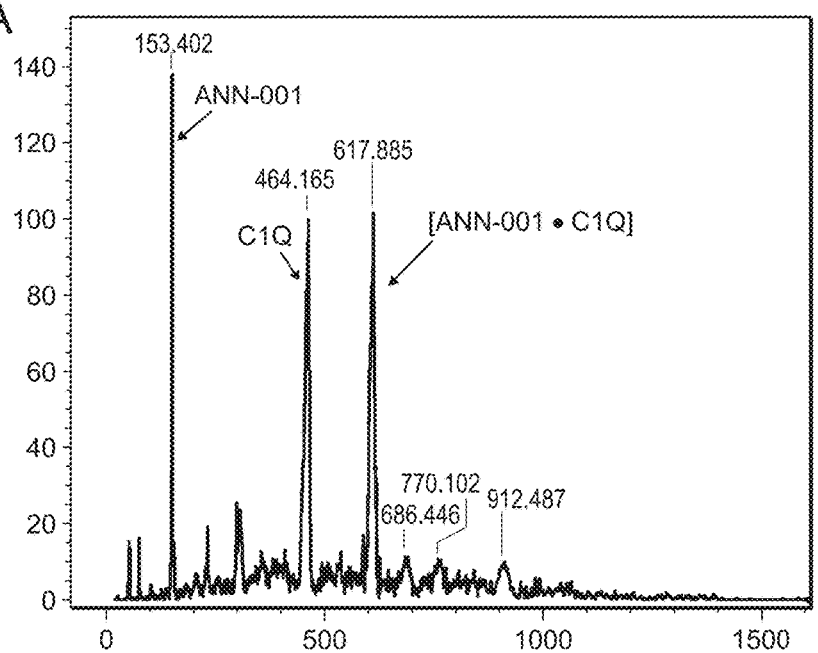
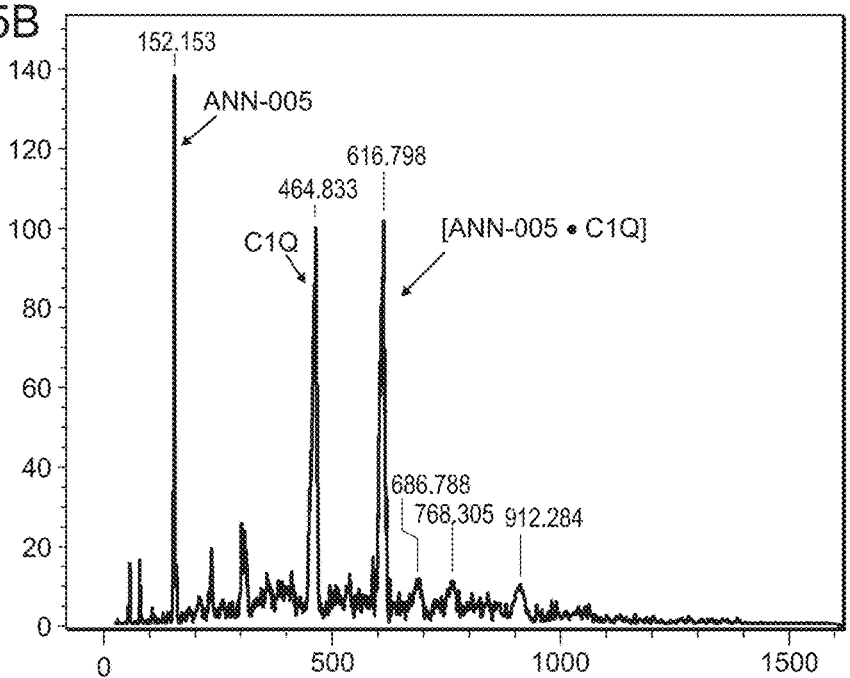

SEQUENCE LISTING

<160> NUMBER OF SEQ ID NOS: 26

<210> SEQ ID NO 1
<211> LENGTH: 245
<212> TYPE: PRT
<213> ORGANISM: Homo sapiens

<400> SEQUENCE: 1

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 2
<211> LENGTH: 253
<212> TYPE: PRT
<213> ORGANISM: Homo sapiens

<400> SEQUENCE: 2

Met Met Met Lys Ile Pro Trp Gly Ser Ile Pro Val Leu Met Leu Leu
1               5                   10                  15

Leu Leu Leu Gly Leu Ile Asp Ile Ser Gln Ala Gln Leu Ser Cys Thr
            20                  25                  30

Gly Pro Pro Ala Ile Pro Gly Ile Pro Gly Ile Pro Gly Thr Pro Gly
        35                  40                  45

Pro Asp Gly Gln Pro Gly Thr Pro Gly Ile Lys Gly Glu Lys Gly Leu
    50                  55                  60

Pro Gly Leu Ala Gly Asp His Gly Glu Phe Gly Glu Lys Gly Asp Pro

```
                65                  70                  75                  80
        Gly Ile Pro Gly Asn Pro Gly Lys Val Gly Pro Lys Gly Pro Met Gly
                            85                  90                  95

Pro Lys Gly Gly Pro Gly Ala Pro Gly Ala Pro Gly Pro Lys Gly Glu
                        100                 105                 110

Ser Gly Asp Tyr Lys Ala Thr Gln Lys Ile Ala Phe Ser Ala Thr Arg
                        115                 120                 125

Thr Ile Asn Val Pro Leu Arg Arg Asp Gln Thr Ile Arg Phe Asp His
                    130                 135                 140

Val Ile Thr Asn Met Asn Asn Asn Tyr Glu Pro Arg Ser Gly Lys Phe
        145                 150                 155                 160

Thr Cys Lys Val Pro Gly Leu Tyr Tyr Phe Thr Tyr His Ala Ser Ser
                            165                 170                 175

Arg Gly Asn Leu Cys Val Asn Leu Met Arg Gly Arg Glu Arg Ala Gln
                        180                 185                 190

Lys Val Val Thr Phe Cys Asp Tyr Ala Tyr Asn Thr Phe Gln Val Thr
                        195                 200                 205

Thr Gly Gly Met Val Leu Lys Leu Glu Gln Gly Glu Asn Val Phe Leu
                    210                 215                 220

Gln Ala Thr Asp Lys Asn Ser Leu Leu Gly Met Glu Gly Ala Asn Ser
        225                 230                 235                 240

Ile Phe Ser Gly Phe Leu Leu Phe Pro Asp Met Glu Ala
                            245                 250

<210> SEQ ID NO 3
<211> LENGTH: 245
<212> TYPE: PRT
<213> ORGANISM: Homo sapiens

<400> SEQUENCE: 3

Met Asp Val Gly Pro Ser Ser Leu Pro His Leu Gly Leu Lys Leu Leu
        1               5                   10                  15

Leu Leu Leu Leu Leu Leu Pro Leu Arg Gly Gln Ala Asn Thr Gly Cys
                        20                  25                  30

Tyr Gly Ile Pro Gly Met Pro Gly Leu Pro Gly Ala Pro Gly Lys Asp
                    35                  40                  45

Gly Tyr Asp Gly Leu Pro Gly Pro Lys Gly Glu Pro Gly Ile Pro Ala
                50                  55                  60

Ile Pro Gly Ile Arg Gly Pro Lys Gly Gln Lys Gly Glu Pro Gly Leu
        65                  70                  75                  80

Pro Gly His Pro Gly Lys Asn Gly Pro Met Gly Pro Pro Gly Met Pro
                            85                  90                  95

Gly Val Pro Gly Pro Met Gly Ile Pro Gly Glu Pro Gly Glu Glu Gly
                        100                 105                 110

Arg Tyr Lys Gln Lys Phe Gln Ser Val Phe Thr Val Thr Arg Gln Thr
                        115                 120                 125

His Gln Pro Pro Ala Pro Asn Ser Leu Ile Arg Phe Asn Ala Val Leu
                    130                 135                 140

Thr Asn Pro Gln Gly Asp Tyr Asp Thr Ser Thr Gly Lys Phe Thr Cys
        145                 150                 155                 160

Lys Val Pro Gly Leu Tyr Tyr Phe Val Tyr His Ala Ser His Thr Ala
                            165                 170                 175

Asn Leu Cys Val Leu Leu Tyr Arg Ser Gly Val Lys Val Val Thr Phe
                        180                 185                 190
```

```
Cys Gly His Thr Ser Lys Thr Asn Gln Val Asn Ser Gly Gly Val Leu
            195                 200                 205

Leu Arg Leu Gln Val Gly Glu Glu Val Trp Leu Ala Val Asn Asp Tyr
        210                 215                 220

Tyr Asp Met Val Gly Ile Gln Gly Ser Asp Ser Val Phe Ser Gly Phe
225                 230                 235                 240

Leu Leu Phe Pro Asp
            245

<210> SEQ ID NO 4
<211> LENGTH: 107
<212> TYPE: PRT
<213> ORGANISM: Homo sapiens

<400> SEQUENCE: 4

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Asn Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys
            100                 105

<210> SEQ ID NO 5
<211> LENGTH: 11
<212> TYPE: PRT
<213> ORGANISM: Homo sapiens

<400> SEQUENCE: 5

Arg Ala Ser Lys Ser Ile Asn Lys Tyr Leu Ala
1               5                   10

<210> SEQ ID NO 6
<211> LENGTH: 7
<212> TYPE: PRT
<213> ORGANISM: Homo sapiens

<400> SEQUENCE: 6

Ser Gly Ser Thr Leu Gln Ser
1               5

<210> SEQ ID NO 7
<211> LENGTH: 9
<212> TYPE: PRT
<213> ORGANISM: Homo sapiens

<400> SEQUENCE: 7

Gln Gln His Asn Glu Tyr Pro Leu Thr
1               5

<210> SEQ ID NO 8
<211> LENGTH: 121
<212> TYPE: PRT
<213> ORGANISM: Homo sapiens
```

<400> SEQUENCE: 8

Gln Val Gln Leu Gln Gln Pro Gly Ala Glu Leu Val Lys Pro Gly Ala
1               5                   10                  15

Ser Val Lys Leu Ser Cys Lys Ser Ser Gly Tyr His Phe Thr Ser Tyr
            20                  25                  30

Trp Met His Trp Val Lys Gln Arg Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Ser Val Thr Val Ser Ser
        115                 120

<210> SEQ ID NO 9
<211> LENGTH: 10
<212> TYPE: PRT
<213> ORGANISM: Homo sapiens

<400> SEQUENCE: 9

Gly Tyr His Phe Thr Ser Tyr Trp Met His
1               5                   10

<210> SEQ ID NO 10
<211> LENGTH: 17
<212> TYPE: PRT
<213> ORGANISM: Homo sapiens

<400> SEQUENCE: 10

Val Ile His Pro Asn Ser Gly Ser Ile Asn Tyr Asn Glu Lys Phe Glu
1               5                   10                  15

Ser

<210> SEQ ID NO 11
<211> LENGTH: 12
<212> TYPE: PRT
<213> ORGANISM: Homo sapiens

<400> SEQUENCE: 11

Glu Arg Asp Ser Thr Glu Val Leu Pro Met Asp Tyr
1               5                   10

<210> SEQ ID NO 12
<211> LENGTH: 321
<212> TYPE: PRT
<213> ORGANISM: Homo sapiens

<400> SEQUENCE: 12

Gly Ala Thr Gly Thr Cys Cys Ala Gly Ala Thr Ala Ala Cys Cys Cys
1               5                   10                  15

Ala Gly Thr Cys Thr Cys Cys Ala Thr Cys Thr Thr Ala Thr Cys Thr
            20                  25                  30

Thr Gly Cys Thr Gly Cys Ala Thr Cys Thr Cys Cys Thr Gly Gly Ala
        35                  40                  45

```
Gly Ala Ala Ala Cys Cys Ala Thr Thr Ala Cys Thr Ala Thr Thr Ala
    50                  55                  60

Ala Thr Thr Gly Cys Ala Gly Gly Gly Cys Ala Ala Gly Thr Ala Ala
65                  70                  75                  80

Gly Ala Gly Cys Ala Thr Thr Ala Ala Cys Ala Ala Ala Thr Ala Thr
                85                  90                  95

Thr Thr Ala Gly Cys Cys Thr Gly Gly Thr Ala Thr Cys Ala Ala Gly
            100                 105                 110

Ala Gly Ala Ala Ala Cys Cys Thr Gly Gly Gly Ala Ala Ala Ala Cys
        115                 120                 125

Thr Ala Ala Thr Ala Ala Gly Cys Thr Thr Cys Thr Thr Ala Thr Cys
    130                 135                 140

Thr Ala Cys Thr Cys Thr Gly Gly Ala Thr Cys Cys Ala Cys Thr Thr
145                 150                 155                 160

Thr Gly Cys Ala Ala Thr Cys Thr Gly Gly Ala Ala Thr Thr Cys Cys
                165                 170                 175

Ala Thr Cys Ala Ala Gly Gly Thr Thr Cys Ala Gly Thr Gly Gly Cys
            180                 185                 190

Ala Gly Thr Gly Gly Ala Thr Cys Thr Gly Gly Thr Ala Cys Ala Gly
        195                 200                 205

Ala Thr Thr Thr Cys Ala Cys Thr Cys Thr Cys Ala Cys Cys Ala Thr
    210                 215                 220

Cys Ala Gly Thr Ala Gly Cys Cys Thr Gly Gly Ala Gly Cys Cys Thr
225                 230                 235                 240

Gly Ala Ala Gly Ala Thr Thr Thr Thr Gly Cys Ala Ala Thr Gly Thr
                245                 250                 255

Ala Thr Thr Ala Cys Thr Gly Thr Cys Ala Ala Cys Ala Ala Cys Ala
            260                 265                 270

Thr Ala Ala Thr Gly Ala Ala Thr Ala Cys Cys Cys Gly Cys Thr Cys
        275                 280                 285

Ala Cys Gly Thr Thr Cys Gly Gly Thr Gly Cys Thr Gly Gly Gly Ala
    290                 295                 300

Cys Cys Ala Ala Gly Cys Thr Gly Gly Ala Gly Cys Thr Gly Ala Ala
305                 310                 315                 320

Ala

<210> SEQ ID NO 13
<211> LENGTH: 363
<212> TYPE: PRT
<213> ORGANISM: Homo sapiens
<400> SEQUENCE: 13

Cys Ala Gly Gly Thr Cys Cys Ala Ala Cys Thr Gly Cys Ala Gly Cys
 1               5                  10                  15

Ala Gly Cys Cys Thr Gly Gly Gly Gly Cys Thr Gly Ala Gly Cys Thr
            20                  25                  30

Gly Gly Thr Ala Ala Ala Gly Cys Cys Thr Gly Gly Gly Gly Cys Thr
        35                  40                  45

Thr Cys Ala Gly Thr Gly Ala Ala Gly Thr Thr Gly Thr Cys Cys Thr
    50                  55                  60

Gly Cys Ala Ala Gly Thr Cys Thr Thr Cys Thr Gly Gly Cys Thr Ala
65                  70                  75                  80

Cys Cys Ala Thr Thr Thr Cys Ala Cys Cys Ala Gly Cys Thr Ala Cys
                85                  90                  95
```

Thr Gly Gly Ala Thr Gly Cys Ala Cys Thr Gly Gly Thr Gly Ala
            100                 105                 110

Ala Gly Cys Ala Gly Ala Gly Gly Cys Thr Gly Gly Ala Cys Ala
            115                 120                 125

Ala Gly Gly Cys Cys Thr Thr Gly Ala Gly Thr Gly Gly Ala Thr Thr
            130                 135                 140

Gly Gly Ala Gly Thr Gly Ala Thr Thr Cys Ala Thr Cys Cys Thr Ala
145                 150                 155                 160

Ala Thr Ala Gly Thr Gly Gly Thr Ala Gly Thr Ala Thr Thr Ala Ala
                165                 170                 175

Cys Thr Ala Cys Ala Ala Thr Gly Ala Gly Ala Ala Gly Thr Thr Cys
            180                 185                 190

Gly Ala Gly Ala Gly Cys Ala Ala Gly Gly Cys Cys Ala Cys Ala Cys
            195                 200                 205

Thr Gly Ala Cys Thr Gly Thr Ala Gly Ala Cys Ala Ala Ala Thr Cys
            210                 215                 220

Cys Thr Cys Cys Ala Gly Cys Ala Cys Ala Gly Cys Cys Thr Ala Cys
225                 230                 235                 240

Ala Thr Gly Cys Ala Ala Cys Thr Cys Ala Gly Cys Ala Gly Cys Cys
                245                 250                 255

Thr Gly Ala Cys Ala Thr Cys Thr Gly Ala Gly Gly Ala Cys Thr Cys
            260                 265                 270

Gly Gly Cys Gly Gly Thr Cys Thr Ala Thr Ala Thr Thr Gly Thr
            275                 280                 285

Gly Cys Ala Gly Ala Gly Ala Gly Ala Gly Ala Gly Ala Thr Thr
            290                 295                 300

Cys Thr Ala Cys Gly Gly Ala Gly Gly Thr Thr Cys Thr Cys Cys Cys
305                 310                 315                 320

Thr Ala Thr Gly Gly Ala Cys Thr Ala Cys Thr Gly Gly Gly Gly Thr
                325                 330                 335

Cys Ala Ala Gly Gly Ala Ala Cys Cys Thr Cys Ala Gly Thr Cys Ala
            340                 345                 350

Cys Cys Gly Thr Cys Thr Cys Cys Thr Cys Ala
            355                 360

<210> SEQ ID NO 14
<211> LENGTH: 245
<212> TYPE: PRT
<213> ORGANISM: Mus musculus

<400> SEQUENCE: 14

Met Glu Thr Ser Gln Gly Trp Leu Val Ala Cys Val Leu Thr Met Thr
1               5                   10                  15

Leu Val Trp Thr Val Ala Glu Asp Val Cys Arg Ala Pro Asn Gly Lys
                20                  25                  30

Asp Gly Ala Pro Gly Asn Pro Gly Arg Pro Gly Arg Pro Gly Leu Lys
            35                  40                  45

Gly Glu Arg Gly Glu Pro Gly Ala Ala Gly Ile Arg Thr Gly Ile Arg
        50                  55                  60

Gly Phe Lys Gly Asp Pro Gly Glu Ser Gly Pro Pro Gly Lys Pro Gly
65                  70                  75                  80

Asn Val Gly Leu Pro Gly Pro Ser Gly Pro Leu Gly Asp Ser Gly Pro
                85                  90                  95

Gln Gly Leu Lys Gly Val Lys Gly Asn Pro Gly Asn Ile Arg Asp Gln
            100                 105                 110

```
Pro Arg Pro Ala Phe Ser Ala Ile Arg Gln Asn Pro Met Thr Leu Gly
        115                 120                 125

Asn Val Val Ile Phe Asp Lys Val Leu Thr Asn Gln Glu Ser Pro Tyr
    130                 135                 140

Gln Asn His Thr Gly Arg Phe Ile Cys Ala Val Pro Gly Phe Tyr Tyr
145                 150                 155                 160

Phe Asn Phe Gln Val Ile Ser Lys Trp Asp Leu Cys Leu Phe Ile Lys
                165                 170                 175

Ser Ser Ser Gly Gly Gln Pro Arg Asp Ser Leu Ser Phe Ser Asn Thr
            180                 185                 190

Asn Asn Lys Gly Leu Phe Gln Val Leu Ala Gly Gly Thr Val Leu Gln
        195                 200                 205

Leu Arg Arg Gly Asp Glu Val Trp Ile Glu Lys Asp Pro Ala Lys Gly
210                 215                 220

Arg Ile Tyr Gln Gly Thr Glu Ala Asp Ser Ile Phe Ser Gly Phe Leu
225                 230                 235                 240

Ile Phe Pro Ser Ala
                245

<210> SEQ ID NO 15
<211> LENGTH: 246
<212> TYPE: PRT
<213> ORGANISM: Mus musculus

<400> SEQUENCE: 15

Met Val Val Gly Pro Ser Cys Gln Pro Pro Cys Gly Leu Cys Leu Leu
  1               5                  10                  15

Leu Leu Phe Leu Leu Ala Leu Pro Leu Arg Ser Gln Ala Ser Ala Gly
            20                  25                  30

Cys Tyr Gly Ile Pro Gly Met Pro Gly Met Pro Gly Ala Pro Gly Lys
            35                  40                  45

Asp Gly His Asp Gly Leu Gln Gly Pro Lys Gly Glu Pro Gly Ile Pro
 50                  55                  60

Ala Val Pro Gly Thr Arg Gly Pro Lys Gly Gln Lys Gly Glu Pro Gly
 65                  70                  75                  80

Met Pro Gly His Arg Gly Lys Asn Gly Pro Arg Gly Thr Ser Gly Leu
                85                  90                  95

Pro Gly Asp Pro Gly Pro Arg Gly Pro Pro Gly Glu Pro Gly Val Glu
            100                 105                 110

Gly Arg Tyr Lys Gln Lys His Gln Ser Val Phe Thr Val Thr Arg Gln
            115                 120                 125

Thr Thr Gln Tyr Pro Glu Ala Asn Ala Leu Val Arg Phe Asn Ser Val
130                 135                 140

Val Thr Asn Pro Gln Gly His Tyr Asn Pro Ser Thr Gly Lys Phe Thr
145                 150                 155                 160

Cys Glu Val Pro Gly Leu Tyr Tyr Phe Val Tyr Tyr Thr Ser His Thr
                165                 170                 175

Ala Asn Leu Cys Val His Leu Asn Leu Asn Leu Ala Arg Val Ala Ser
            180                 185                 190

Phe Cys Asp His Met Phe Asn Ser Lys Gln Val Ser Ser Gly Gly Val
            195                 200                 205

Leu Leu Arg Leu Gln Arg Gly Asp Glu Val Trp Leu Ser Val Asn Asp
210                 215                 220

Tyr Asn Gly Met Val Gly Ile Glu Gly Ser Asn Ser Val Phe Ser Gly
```

```
225                 230                 235                 240

Phe Leu Leu Phe Pro Asp
                245

<210> SEQ ID NO 16
<211> LENGTH: 31
<212> TYPE: PRT
<213> ORGANISM: Homo sapiens

<400> SEQUENCE: 16

Gly Leu Phe Gln Val Val Ser Gly Gly Met Val Leu Gln Leu Gln Gln
  1               5                  10                  15

Gly Asp Gln Val Trp Val Glu Lys Asp Pro Lys Lys Gly His Ile
             20                  25                  30

<210> SEQ ID NO 17
<211> LENGTH: 26
<212> TYPE: PRT
<213> ORGANISM: Homo sapiens

<400> SEQUENCE: 17

Gly Leu Phe Gln Val Val Ser Gly Gly Met Val Leu Gln Leu Gln Gln
  1               5                  10                  15

Gly Asp Gln Val Trp Val Glu Lys Asp Pro
             20                  25

<210> SEQ ID NO 18
<211> LENGTH: 20
<212> TYPE: PRT
<213> ORGANISM: Homo sapiens

<400> SEQUENCE: 18

Ser Gly Gly Met Val Leu Gln Leu Gln Gln Gly Asp Gln Val Trp Val
  1               5                  10                  15

Glu Lys Asp Pro
             20

<210> SEQ ID NO 19
<211> LENGTH: 18
<212> TYPE: PRT
<213> ORGANISM: Homo sapiens

<400> SEQUENCE: 19

Ser Gly Gly Met Val Leu Gln Leu Gln Gln Gly Asp Gln Val Trp Val
  1               5                  10                  15

Glu Lys

<210> SEQ ID NO 20
<211> LENGTH: 23
<212> TYPE: PRT
<213> ORGANISM: Homo sapiens

<400> SEQUENCE: 20

Trp Leu Ala Val Asn Asp Tyr Tyr Asp Met Val Gly Ile Gln Gly Ser
  1               5                  10                  15

Asp Ser Val Phe Ser Gly Phe
             20

<210> SEQ ID NO 21
<211> LENGTH: 16
<212> TYPE: PRT
<213> ORGANISM: Homo sapiens
```

```
<400> SEQUENCE: 21

Tyr Asp Met Val Gly Ile Gln Gly Ser Asp Ser Val Phe Ser Gly Phe
1               5                   10                  15

<210> SEQ ID NO 22
<211> LENGTH: 8
<212> TYPE: PRT
<213> ORGANISM: Homo sapiens

<400> SEQUENCE: 22

Tyr Asp Met Val Gly Ile Gln Gly
1               5

<210> SEQ ID NO 23
<211> LENGTH: 23
<212> TYPE: PRT
<213> ORGANISM: Homo sapiens

<400> SEQUENCE: 23

His Thr Ala Asn Leu Cys Val Leu Leu Tyr Arg Ser Gly Val Lys Val
1               5                   10                  15

Val Thr Phe Cys Gly His Thr
            20

<210> SEQ ID NO 24
<211> LENGTH: 9
<212> TYPE: PRT
<213> ORGANISM: Homo sapiens

<400> SEQUENCE: 24

Arg Ser Gly Val Lys Val Val Thr Phe
1               5

<210> SEQ ID NO 25
<211> LENGTH: 24
<212> TYPE: PRT
<213> ORGANISM: Homo sapiens

<400> SEQUENCE: 25

Gly Leu Phe Gln Val Val Ser Gly Gly Met Val Leu Gln Leu Gln Gln
1               5                   10                  15

Gly Asp Gln Val Trp Val Glu Lys
            20

<210> SEQ ID NO 26
<211> LENGTH: 12
<212> TYPE: PRT
<213> ORGANISM: Homo sapiens

<400> SEQUENCE: 26

Phe Gln Val Val Ser Gly Gly Met Val Leu Gln Leu
1               5                   10
```

ANTI-COMPLEMENT FACTOR C1Q ANTIBODIES AND USES THEREOF

CROSS REFERENCES TO RELATED APPLICATIONS

This application is a continuation application of U.S. application Ser. No. 14/989,038, filed Jan. 6, 2016, which is a continuation application of PCT/US14/046042, filed Jul. 9, 2014, which claims the benefit of U.S. Provisional Application No. 61/844,369, filed Jul. 9, 2013, and U.S. Provisional Application No. 61/871,813, filed Aug. 29, 2013. The entire contents of U.S. application Ser. No. 14/989,038, PCT/US14/046042, U.S. Provisional Application No. 61/844,369, and U.S. Provisional Application No. 61/871,813 are hereby incorporated herein in their entirety by this reference.

GOVERNMENT GRANTS

This invention was made with government support under Grant Number R43AG043302, awarded by the National Institute On Aging of the National Institutes of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717192000640SeqList.txt, date recorded: Jul. 9, 2014, size: 21 KB).

BACKGROUND

1. Field

The present disclosure relates to anti-C1q antibodies and methods of using the same.

2. Description of Related Art

Excessive complement activation has been associated with a range of disease conditions, including numerous inflammatory and autoimmune diseases. More recently, the complement system has also been shown to contribute to neurodegenerative disease pathology. Specifically, complement factors, such as C1q, were shown to be expressed in neuronal synapses and to mark these synapses for elimination. See, e.g., U.S. Patent Publication Nos. 2012/0195880 and 2012/328601. While selective synapse loss is an essential aspect of normal brain development ("synaptic pruning"), excessive synapse loss, especially in a mature or aging brain, results in neurodegeneration and cognitive decline. Elevated synaptic complement expression was found to contribute to synaptic loss in normal aging and in neurodegenerative disease progression. Conversely, lowering neuronal complement expression was found to be neuroprotective. Based on these findings, neutralizing the activity of complement factors such as C1q is regarded as a promising therapeutic strategy to prevent synapse loss and to slow neurodegenerative disease progression as well as cognitive decline in normal aging.

Neurodegenerative diseases involving synapse loss and considered to be amenable to treatments aiming at the neutralization of complement factors such as C1q include Alzheimer's disease, amyotrophic lateral sclerosis, multiple sclerosis, glaucoma, myotonic dystrophy, Down syndrome, Parkinson's disease, Huntington's disease, and the like.

Only a limited number of complement neutralizing antibodies are known to date (see, e.g., Klos A. et al., Mol Immunol. 2009, 46(14), 2753-2766; Carroll S. & Georgiou G., Immunobiology 2013, 218(8), 1041-1048; Tuzun et al., J. Neuroimmunol. 2007, 182, 167-176; Nelson et al., J. Clin. Invest. 2006, 116:2892-2900; Heinz et al., J. Immunol. 1984, 133, 400-404; Jiang et al., J. Immunol. 1991, 146, 2324-2330; Trinder et al., Scand. J. Immunol. 1999, 50, 635-641; Hwang et al., Mol. Immunol. 2008, 45, 2570-2580). Only the C5 neutralizing antibody Eculizumab, an inhibitor of the terminal complement activation pathway, has obtained regulatory approval to date; Eculizumab is marketed for the treatment of paroxysmal nocturnal hemoglobinuria (PNH; Hillmen et al., N Engl J Med. 2006, 355(12):1233-43).

Thus, there is a need to develop further antibodies that specifically bind to and neutralize biological activities of complement factors such as C1q.

All references cited herein, including patent applications and publications, are hereby incorporated by reference in their entirety.

BRIEF SUMMARY

Provided herein are anti-C1q antibodies and methods of using anti-C1q antibodies.

In certain aspects, this disclosure provides for an isolated anti-C1q antibody comprising a light chain variable domain and a heavy chain variable domain, wherein the light chain variable domain comprises the HVR-L1, HVR-L2, and HVR-L3 of the monoclonal antibody M1 produced by a hybridoma cell line deposited with Accession Number PTA-120399 or progeny thereof; and/or wherein the heavy chain variable domain comprises the HVR-H1, HVR-H2, and HVR-H3 of the monoclonal antibody M1 produced by a hybridoma cell line deposited with ATCC Accession Number PTA-120399 or progeny thereof.

In certain aspects, the present disclosure provides for an isolated antibody that specifically binds to a C1q protein, wherein the antibody comprises a light chain HVR selected from the group consisting of HVR-L1 comprising the amino acid sequence of SEQ ID NO:5, HVR-L2 comprising the amino acid sequence of SEQ ID NO:6, and HVR-L3 comprising the amino acid sequence of SEQ ID NO:7; and/or wherein the antibody comprises a heavy chain HVR selected from the group consisting of HVR-H1 comprising the amino acid sequence of SEQ ID NO:9, HVR-H2 comprising the amino acid sequence of SEQ ID NO:10, and HVR-H3 comprising the amino acid sequence of SEQ ID NO:11. In some embodiments that may be combined with any of the preceding embodiments, the antibody comprises HVR-L1 comprising the amino acid sequence of SEQ ID NO:5, HVR-L2 comprising the amino acid sequence of SEQ ID NO:6, and HVR-L3 comprising the amino acid sequence of SEQ ID NO:7; and/or wherein the antibody comprises HVR-H1 comprising the amino acid sequence of SEQ ID NO:9, HVR-H2 comprising the amino acid sequence of SEQ ID NO:10, and HVR-H3 comprising the amino acid sequence of SEQ ID NO:11. In some embodiments that may be combined with any of the preceding embodiments, the antibody comprises a light chain variable domain comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO:4. In some embodiments that may be combined with any of the preceding embodiments, the antibody comprises a heavy chain variable domain comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO:8.

In certain aspects, the present disclosure provides for an isolated murine anti-human C1q monoclonal antibody M1 produced by a hybridoma cell line deposited with ATCC Accession Number PTA-120399, or progeny thereof.

In some embodiments that may be combined with any of the preceding embodiments, the antibody binds specifically to both human C1q and mouse C1q. In some embodiments that may be combined with any of the preceding embodiments, the antibody binds specifically to rat C1q. In some embodiments that may be combined with any of the preceding embodiments, the antibody binds specifically to human C1q, mouse C1q, and rat C1q. In some embodiments that may be combined with any of the preceding embodiments, the antibody has dissociation constant ($K_D$) for human C1q and mouse C1q that ranges from less than about 30 nM to less than about 100 pM. In some embodiments that may be combined with any of the preceding embodiments, the antibody has dissociation constant ($K_D$) for human C1q and mouse C1q of less than about 30 nM. In some embodiments that may be combined with any of the preceding embodiments, the antibody has dissociation constant ($K_D$) for human C1q and mouse C1q of less than about 20 nM. In some embodiments that may be combined with any of the preceding embodiments, the antibody has dissociation constant ($K_D$) for human C1q and mouse C1q of less than about 10 nM. In some embodiments that may be combined with any of the preceding embodiments, the antibody has dissociation constant ($K_D$) for human C1q and mouse C1q of less than about 5 nM. In some embodiments that may be combined with any of the preceding embodiments, the antibody has dissociation constant ($K_D$) for human C1q and mouse C1q of less than about 1 nM. In some embodiments that may be combined with any of the preceding embodiments, the antibody has dissociation constants ($K_D$) for human C1q and mouse C1q of less than 100 pM or less than about 100 pM. In some embodiments that may be combined with any of the preceding embodiments, the antibody specifically binds to and neutralizes a biological activity of C1q. In some embodiments that may be combined with any of the preceding embodiments, the biological activity of C1q is (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to B-amyloid, or (10) C1q binding to calreticulin. In some embodiments that may be combined with any of the preceding embodiments, the biological activity of C1q is (1) activation of the classical complement activation pathway, (2) activation of antibody and complement dependent cytotoxicity, (3) CH50 hemolysis, (4) synapse loss, (5) B-cell antibody production, (6) dendritic cell maturation, (7) T-cell proliferation, (8) cytokine production (9) microglia activation, (10) Arthus reaction, (11) phagocytosis of synapses or nerve endings or (12) activation of complement receptor 3 (CR3/C3) expressing cells. In some embodiments that may be combined with any of the preceding embodiments, CH50 hemolysis comprises human, mouse, and/or rat CH50 hemolysis. In some embodiments that may be combined with any of the preceding embodiments, the antibody is capable of neutralizing at least 50%, at least 80%, or at least 90% of CH50 hemolysis. In some embodiments that may be combined with any of the preceding embodiments, the antibody is capable of neutralizing at least 50% of CH50 hemolysis at a dose of less than 200 ng/ml, less than 100 ng/ml, less than 50 ng/ml, or less than 20 ng/ml. In some embodiments that may be combined with any of the preceding embodiments, the antibody is a murine antibody. In some embodiments that may be combined with any of the preceding embodiments, the antibody is a humanized or chimeric antibody.

In certain aspects, the present disclosure provides for an isolated anti-C1q antibody which binds essentially the same C1q epitope as the antibody M1 produced by the hybridoma cell line with ATCC Accession Number PTA-120399 or anti-C1q binding fragments thereof. In some embodiments, the antibody comprises a light chain variable domain comprising an HVR-L1 comprising the amino acid sequence of SEQ ID NO:5, an HVR-L2 comprising the amino acid sequence of SEQ ID NO:6, and an HVR-L3 comprising the amino acid sequence of SEQ ID NO:7. In some embodiments, the light chain variable domain comprises a light chain variable domain comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO:4. In some embodiments, the antibody comprises a heavy chain variable domain comprising an HVR-H1 comprising the amino acid sequence of SEQ ID NO:9, an HVR-H2 comprising the amino acid sequence of SEQ ID NO:10, and an HVR-H3 comprising the amino acid sequence of SEQ ID NO:11. In some embodiments, the heavy chain variable domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO:8.

In certain aspects, the present disclosure provides an isolated anti-C1q antibody, which binds to a C1q protein and binds to one or more amino acids of the C1q protein within amino acid residues selected from the group consisting of: i. amino acid residues 96-226 of SEQ ID NO:1 (SEQ ID NO:16), or amino acid residues of a C1q protein chain A (C1qA) corresponding to amino acid residues 196-226 (GLFQVVSGGMVLQLQQGDQVWVEKDPKKGHI) of SEQ ID NO:1 (SEQ ID NO:16); ii. amino acid residues 196-221 of SEQ ID NO:1 (SEQ ID NO:17), or amino acid residues of a C1qA corresponding to amino acid residues 196-221 (GLFQVVSGGMVLQLQQGDQVWVEKDP) of SEQ ID. NO:1 (SEQ ID NO:17); iii. amino acid residues 202-221 of SEQ ID NO:1 (SEQ ID NO:18), or amino acid residues of a C1qA corresponding to amino acid residues 202-221 (SGGMVLQLQQGDQVWVEKDP) of SEQ ID NO:1 (SEQ ID NO:18); iv. amino acid residues 202-219 of SEQ ID NO:1 (SEQ ID NO:19), or amino acid residues of a C1qA corresponding to amino acid residues 202-219 SGGMVLQLQQGDQVWVEK of SEQ ID NO:1 (SEQ ID NO:19); and v. amino acid residues Lys 219 and/or Ser 202 of SEQ ID NO:1, or amino acid residues of a C1qA corresponding Lys 219 and/or Ser 202 of SEQ ID NO:1. In some embodiments, the antibody further binds to one or more amino acids of the C1q protein within amino acid residues selected from the group consisting of: (a) amino acid residues 218-240 of SEQ ID NO:3 (SEQ ID NO:20) or amino acid residues of a C1q protein chain C (C1qC) corresponding to amino acid residues 218-240 (WLAVNDYYDMVGI QGSDSVFSGF) of SEQ ID NO:3 (SEQ ID NO:20); (b) amino acid residues 225-240 of SEQ ID NO:3 (SEQ ID NO:21) or amino acid residues of a C1qC corresponding to amino acid residues 225-240 (YDMVGI QGSDSVFSGF) of SEQ ID NO:3 (SEQ ID NO:21); (c) amino acid residues 225-232 of SEQ ID NO:3 (SEQ ID NO:22) or amino acid residues of a C1qC corresponding to amino acid residues 225-232 (YDMVGIQG) of SEQ ID NO:3 (SEQ ID NO:22); (d) amino acid residue Tyr 225 of SEQ ID NO:3 or an amino acid residue of a C1qC corresponding to amino acid residue Tyr 225 of SEQ ID NO:3; (e) amino acid residues 174-196 of SEQ ID NO:3 (SEQ ID NO:23) or amino acid residues of a C1qC corresponding to amino acid residues 174-196 (HTANLCVLLYRSGVKVVTFCGHT) of SEQ ID NO:3 (SEQ ID NO:23); (f) amino acid residues 184-192 of SEQ ID NO:3 (SEQ ID NO:24) or amino acid residues of a C1qC corresponding to amino acid residues 184-192 (RSGVKVVTF) of SEQ ID NO:3 (SEQ ID NO:24); (g) amino acid residues 185-187 of SEQ ID NO:3 or amino acid residues of a C1qC corresponding to amino acid residues 185-187 (SGV) of SEQ ID NO:3; and (h) amino acid residue Ser 185 of SEQ ID NO:3 or an amino acid residue of a C1qC corresponding to amino acid residue Ser 185 of SEQ ID NO:3. In certain embodiments, the antibody is a humanized antibody, a chimeric antibody, or a human antibody. In certain embodiments, the antibody binds to amino acid residue Lys 219 and Ser 202 of the human C1qA as shown in SEQ ID NO:1 or amino acids of a human C1qA corresponding to Lys 219 and Ser 202 as shown in SEQ ID NO:1, and amino acid residue Tyr 225 of the human C1qC as shown in SEQ ID NO:3 or an amino acid residue of a human C1qC corresponding to Tyr 225 as shown in SEQ ID NO:3. In certain embodiments, the antibody binds to amino acid residue Lys 219 of the human C1qA as shown in SEQ ID NO:1 or an amino acid residue of a human C1qA corresponding to Lys 219 as shown in SEQ ID NO:1, and amino acid residue Ser 185 of the human C1qC as shown in SEQ ID NO:3 or an amino acid residue of a human C1qC corresponding to Ser 185 as shown in SEQ ID NO:3.

In certain aspects, the present disclosure provides an isolated anti-C1q antibody, which binds to a C1q protein and binds to one or more amino acids of the C1q protein within amino acid residues selected from the group consisting of: (a) amino acid residues 218-240 of SEQ ID NO:3 (SEQ ID NO:20) or amino acid residues of a C1qC corresponding to amino acid residues 218-240 (WLAVNDYYDMVGI QGSDSVFSGF) of SEQ ID NO:3 (SEQ ID NO:20); (b) amino acid residues 225-240 of SEQ ID NO:3 (SEQ ID NO:21) or amino acid residues of a C1qC corresponding to amino acid residues 225-240 (YDMVGI QGSDSVFSGF) of SEQ ID NO:3 (SEQ ID NO:21); (c) amino acid residues 225-232 of SEQ ID NO:3 (SEQ ID NO:22) or amino acid residues of a C1qC corresponding to amino acid residues 225-232 (YDMVGIQG) of SEQ ID NO:3 (SEQ ID NO:22); (d) amino acid residue Tyr 225 of SEQ ID NO:3 or an amino acid residue of a C1qC corresponding to amino acid residue Tyr 225 of SEQ ID NO:3; (e)amino acid residues 174-196 of SEQ ID NO:3 (SEQ ID NO:23) or amino acid residues of a C1qC corresponding to amino acid residues 174-196 (HTANLCVLLYRSGVKVVTFCGHT) of SEQ ID NO:3 (SEQ ID NO:23); (f) amino acid residues 184-192 of SEQ ID NO:3 (SEQ ID NO:24) or amino acid residues of a C1qC corresponding to amino acid residues 184-192 (RSGVKVVTF) of SEQ ID NO:3 (SEQ ID NO:24); (g) amino acid residues 185-187 of SEQ ID NO:3 or amino acid residues of a C1qC corresponding to amino acid residues 185-187 (SGV) of SEQ ID NO:3; and (h) amino acid residue Ser 185 of SEQ ID NO:3 or an amino acid residue of a C1qC corresponding to amino acid residue Ser 185 of SEQ ID NO:3. In certain embodiments, the antibody is a humanized antibody, a chimeric antibody, or a human antibody. In certain embodiments, the antibody binds to amino acid residue Lys 219 and Ser 202 of the human C1qA as shown in SEQ ID NO:1 or amino acids of a human C1qA corresponding to Lys 219 and Ser 202 as shown in SEQ ID NO:1, and amino acid residue Tyr 225 of the human C1qC as shown in SEQ ID NO:3 or an amino acid residue of a human C1qC corresponding to Tyr 225 as shown in SEQ ID NO:3. In certain embodiments, the antibody binds to amino acid residue Lys 219 of the human C1qA as shown in SEQ ID NO:1 or an amino acid residue of a human C1qA corresponding to Lys 219 as shown in SEQ ID NO:1, and amino acid residue Ser 185 of the human C1qC as shown in SEQ ID NO:3 or an amino acid residue of a human C1qC corresponding to Ser 185 as shown in SEQ ID NO:3.

In some embodiments that may be combined with any of the preceding embodiments, the antibody is a humanized antibody, a chimeric antibody, or a human antibody. In some embodiments that may be combined with any of the preceding embodiments, the antibody binds specifically to both human C1q and mouse C1q. In some embodiments that may be combined with any of the preceding embodiments, the antibody binds specifically to rat C1q. In some embodiments that may be combined with any of the preceding embodiments, the antibody binds specifically to human C1q, mouse C1q, and rat C1q. In some embodiments that may be combined with any of the preceding embodiments, the antibody has dissociation constant ($K_D$) for human C1q and mouse C1q that ranges from less than about 30 nM to less than about 100 pM. In some embodiments that may be combined with any of the preceding embodiments, the antibody has dissociation constant ($K_D$) for human C1q and mouse C1q of less than about 30 nM. In some embodiments that may be combined with any of the preceding embodiments, the antibody has dissociation constant ($K_D$) for human C1q and mouse C1q of less than about 20 nM. In some embodiments that may be combined with any of the preceding embodiments, the antibody has dissociation constant ($K_D$) for human C1q and mouse C1q of less than about 10 nM. In some embodiments that may be combined with any of the preceding embodiments, the antibody has dissociation constant ($K_D$) for human C1q and mouse C1q of less than about 5 nM. In some embodiments that may be combined with any of the preceding embodiments, the antibody has dissociation constant ($K_D$) for human C1q and mouse C1q of less than about 1 nM. In some embodiments that may be combined with any of the preceding embodiments, the antibody has dissociation constants ($K_D$) for human C1q and mouse C1q of less than 100 pM or less than about 100 pM. In some embodiments that may be combined with any of the preceding embodiments, the antibody specifically binds to and neutralizes a biological activity of C1q. In some embodiments that may be combined with any of the preceding embodiments, the biological activity is (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to beta-amyloid, or (10) C1q binding to calreticulin. In some embodiments that may be combined with any of the preceding embodiments, the biological activity is (1) activation of the classical complement activation pathway, (2) activation of antibody and complement dependent cytotoxicity, (3) CH50 hemolysis, (4) synapse loss, (5) B-cell antibody production, (6) dendritic cell maturation, (7) T-cell proliferation, (8) cytokine production (9) microglia activation, (10) Arthus reaction, (11) phagocytosis of synapses or nerve endings, or (12) activation of complement receptor 3 (CR3/C3) expressing cells. In some embodiments that may be combined with any of the preceding embodiments, CH50 hemolysis comprises human, mouse, and/or rat CH50 hemolysis. In some embodiments that may be combined with any of the preceding embodiments, the antibody is capable of neutralizing at least 50%, at least 80%, or at least 90% of CH50 hemolysis. In some embodiments that may be combined with any of the preceding embodiments, the antibody is capable of neutralizing at least 50% of CH50 hemolysis at a dose of less than 200 ng/ml, less than 100 ng/ml, less than 50 ng/ml, or less than 20 ng/ml.

In some embodiments that may be combined with any of the preceding embodiments, the antibody is a bispecific antibody. In some embodiments that may be combined with any of the preceding embodiments, the antibody has been engineered to increase brain penetration. In some embodiments that may be combined with any of the preceding embodiments, the antibody is a bispecific antibody recognizing a first antigen and a second antigen. In some embodiments that may be combined with any of the preceding embodiments, the first antigen is a C1q protein and the second antigen is an antigen facilitating transport across the blood-brain-barrier. In some embodiments that may be combined with any of the preceding embodiments, the second antigen is selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005. In some embodiments that may be combined with any of the preceding embodiments, the antibody is of the IgG class. In some embodiments that may be combined with any of the preceding embodiments, the antibody has an $IgG_1$, $IgG_2$, $IgG_3$, or $IgG_4$ isotype. In some embodiments that may be combined with any of the preceding embodiments, the antibody is an antibody fragment. In some embodiments that may be combined with any of the preceding embodiments, the antibody is a Fab, $F(ab')_2$, or Fab' fragment. In some embodiments that may be combined with any of the preceding embodiments, the antibody fragment specifically binds to and neutralizes a biological activity of C1q. In some embodiments that may be combined with any of the preceding embodiments, the antibody fragment has better brain penetration as compared to its corresponding full-length antibody. In some embodiments that may be combined with any of the preceding embodiments, the antibody fragment has a shorter half-life as compared to its corresponding full-length antibody.

In certain aspects, the present disclosure provides for an isolated polynucleotide comprising a nucleic acid sequence encoding an antibody of this disclosure. In certain aspects, the present disclosure provides for an isolated polynucleotide comprising a nucleic acid sequence encoding an anti-C1q antibody of any of the preceding embodiments. In certain aspects, the present disclosure provides for an isolated host cell comprising a nucleic acid sequence of this disclosure. In certain aspects, the present disclosure provides for an isolated host cell comprising a nucleic acid sequence of any of the preceding embodiments. In certain aspects, the present disclosure provides for a hybridoma cell deposited with ATCC Accession Number PTA-120399, or progeny thereof. In certain aspects, the present disclosure provides for a pharmaceutical composition comprising an antibody of this disclosure and a pharmaceutically acceptable carrier. In certain aspects, the present disclosure provides for a pharmaceutical composition comprising an anti-C1q antibody of any of the preceding embodiments and a pharmaceutically acceptable carrier.

In certain aspects, the present disclosure provides for a method of treating or preventing a disease associated with complement activation in an individual in need of such treatment, the method comprising the step of administering a therapeutically effective dose of an antibody of this disclosure. In certain aspects, the present disclosure provides for a method of treating or preventing a disease associated with complement activation in an individual in need of such treatment, the method comprising the step of administering a therapeutically effective dose of an anti-C1q antibody of any of the preceding embodiments. In other aspects, the present disclosure provides an anti-C1q antibody of any of the preceding embodiments for use in treating or preventing a disease associated with complement activation in an individual in need of such treatment. In other aspects, the present disclosure provides use of an anti-C1q antibody of any of the preceding embodiments in the manufacture of a medicament for treating or preventing a disease associated with complement activation in an individual in need of such treatment.

In some embodiments that may be combined with any of the preceding embodiments, the disease associated with complement activation is a neurodegenerative disorder. In some embodiments that may be combined with any of the preceding embodiments, the neurodegenerative disorder is associated with the loss of synapses or nerve connections. In some embodiments that may be combined with any of the preceding embodiments, the neurodegenerative disorder is associated with synapse loss that is dependent on the complement receptor 3(CR3)/C3 or complement receptor CR1. In some embodiments that may be combined with any of the preceding embodiments, the neurodegenerative disorder is associated with pathological activity-dependent synaptic pruning. In some embodiments that may be combined with any of the preceding embodiments, the neurodegenerative disorder is associated with synapse phagocytosis by microglia. In some embodiments that may be combined with any of the preceding embodiments, the neurodegenerative disorder is Alzheimer's disease amyotrophic lateral sclerosis, multiple sclerosis, glaucoma, myotonic dystrophy, Down syndrome, Parkinson's disease, or Huntington's disease. In some embodiments that may be combined with any of the preceding embodiments, the disease associated with complement activation is an inflammatory disease, an autoimmune disease, or metabolic disorder. In some embodiments that may be combined with any of the preceding embodiments, the inflammatory disease, autoimmune disease, or metabolic disorder is diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases, age-related macular degeneration (AMD), choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, allo-transplantation, hyperacute rejection, hemodialysis, chronic occlusive pulmonary distress syndrome (COPD), asthma, or aspiration pneumonia. In some embodiments that may be combined with any of the preceding embodiments, the disease associated with complement activation is an autoimmune disease selected from the group consisting of myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, polymyalgia rheumatica, temporal arteritis, and Wegener's granulomatosis.

In certain aspects, the present disclosure provides for a kit comprising an anti-C1q antibody of any of the preceding embodiments, and a package insert comprising instructions for using the antibody to treat or prevent a disease associated with complement activation in an individual in need of such treatment. In some embodiments, the disease associated with complement activation is a neurodegenerative disorder. In some embodiments, the neurodegenerative disorder is associated with loss of synapses or loss nerve connections. In some embodiments, the neurodegenerative disorder is associated with synapse loss that is dependent on the complement receptor 3(CR3)/C3 or complement receptor CR1. In some embodiments, the neurodegenerative disorder is associated with pathological activity-dependent synaptic pruning. In some embodiments, the neurodegenerative disorder is associated with synapse phagocytosis by microglia. In some embodiments, the neurodegenerative disorder is selected from the group consisting of Alzheimer's disease, amyotrophic lateral sclerosis, multiple sclerosis, glaucoma, myotonic dystrophy, Down syndrome, Parkinson's disease, and Huntington's disease. In some embodiments, the disease associated with complement activation is an inflammatory disease, autoimmune disease, or metabolic disorder. In some embodiments, the inflammatory disease, autoimmune disease, or metabolic disorder is selected from the group consisting of diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases, age-related macular degeneration (AMD), choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, allo-transplantation, hyperacute rejection, hemodialysis, chronic occlusive pulmonary distress syndrome (COPD), asthma, and aspiration pneumonia. In some embodiments, the disease associated with complement activation is an autoimmune disease selected from the group consisting of myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, polymyalgia rheumatica, temporal arteritis, and Wegener's granulomatosis.

In certain aspects, the present disclosure provides for a diagnostic kit comprising an antibody of this disclosure. In certain aspects, the present disclosure provides for a kit comprising an anti-C1q antibody of any of the preceding embodiments. In some embodiments, the kit is for diagnostic or therapeutic uses as disclosed herein.

In certain aspects, the present disclosure provides for a method of detecting synapses in an individual having a neurodegenerative disease or autoimmune disease, the method comprising a) administering an antibody of this disclosure to the individual, and b) detecting antibody bound to synapses, thereby detecting synapses in the individual. In other aspects, the present disclosure provides a method of detecting synapses in an individual, by a) administering an anti-C1q antibody of any of the preceding embodiments to the individual, and b) detecting antibody bound to synapses, thereby detecting synapses in the individual. In other aspects, the present disclosure provides an anti-C1q antibody of any of the preceding embodiments for use in detecting synapses in an individual. In other aspects, the present disclosure provides use of an anti-C1q antibody of any of the preceding embodiments in the manufacture of a medicament for detecting synapses in an individual. In some embodiments that may be combined with any of the preceding embodiments, the antibody bound to synapses is detected using imaging techniques selected from the group consisting of positron emission tomography (PET), X-ray computed tomography, single-photon emission computed tomography (SPECT), computed tomography (CT), and computed axial tomography (CAT). In some embodiments that may be combined with any of the preceding embodiments, the detection of antibody bound to synapses provides a quantitative measure of the number of synapses in the individual. In some embodiments that may be combined with any of the preceding embodiments, the individual has a neurodegenerative disease or autoimmune disease. In some embodiments that may be combined with any of the preceding embodiments, the number of synapses in the individual is measured repeatedly over a period of time and a loss of synapses in the individual is detected over time. In some embodiments that may be combined with any of the preceding embodiments, the loss of synapses over time is a measure for the efficacy of a treatment for the neurodegenerative disease or autoimmune disease.

In certain aspects, the present disclosure provides for a method of detecting synapses in a biological sample, the method comprising a) contacting the biological sample with an antibody of this disclosure and b) detecting antibody bound to synapses, thereby detecting synapses in the biological sample. In certain aspects, the present disclosure provides for a method of detecting synapses in a biological sample, the method comprising a) contacting the biological sample with an antibody of this disclosure and b) detecting antibody bound to synapses, thereby detecting synapses in the biological sample. In other aspects, the present disclosure provides a method of detecting synapses in a biological sample, by a) contacting the biological sample with an anti-C1q antibody of any of the preceding embodiments, and b) detecting antibody bound to synapses, thereby detecting synapses in the individual.

In some embodiments that may be combined with any of the preceding embodiments, the method further comprises a step before step a) of obtaining the biological sample from an individual. In some embodiments that may be combined with any of the preceding embodiments, the biological sample comprises a biopsy specimen, a tissue, or a cell. In some embodiments that may be combined with any of the preceding embodiments, the antibody is detected by immunofluorescence microscopy, immunocytochemistry, immunohistochemistry, ELISA, FACS analysis or immunoprecipitation.

It is to be understood that one, some, or all of the properties of the various embodiments described herein may be combined to form other embodiments of the compositions and methods provided herein. These and other aspects of the compositions and methods provided herein will become apparent to one of skill in the art.

DESCRIPTION OF THE FIGURES

FIG. 4A illustrates results from a human CH50 hemolytic assay. FIG. 4B illustrates results from a mouse CH50 hemolytic assay. FIG. 4C illustrates results from a rat CH50 hemolytic assay.

FIG. 5A and FIG. 5B illustrate mass spectrometry characterization of C1q antibody complexes. FIG. 5A shows a mixture of ANN-001 (4A4B11) and C1q shows that ANN-001 monomer at the predicted mass of ~150 kDa, C1q monomer at the expected mass of ~460 kDa, and the C1q/ANN-001 1:1 complex at the predicted mass of ~600 kDa. FIG. 5B shows a mixture of ANN-005 (M1) and C1q shows that ANN-005 monomer at the predicted mass of ~150 kDa, C1q monomer at the expected mass of ~460 kDa, and the C1q/ANN-005 1:1 complex at the predicted mass of ~600 kDa.

FIG. 6A depicts C1q and ANN-005 mixed in equimolar concentrations and incubated in the absence of a mixture of C1q peptides. FIG. 6B depicts C1q and ANN-005 mixed in equimolar concentrations and incubated in the presence of a mixture of C1q peptides generated by pepsin digestion of C1q and analyzed by mass spectrometry. In each case, a portion of the unbound antibody and antigen (ANN-005 and C1q) can be identified at the expected masses for monomers (~150 kDa and ~460 kDa respectively) and a 1:1 complex is present at a mass of ~615 kDa.

DETAILED DESCRIPTION OF THE INVENTION

General Techniques

Figure 1:
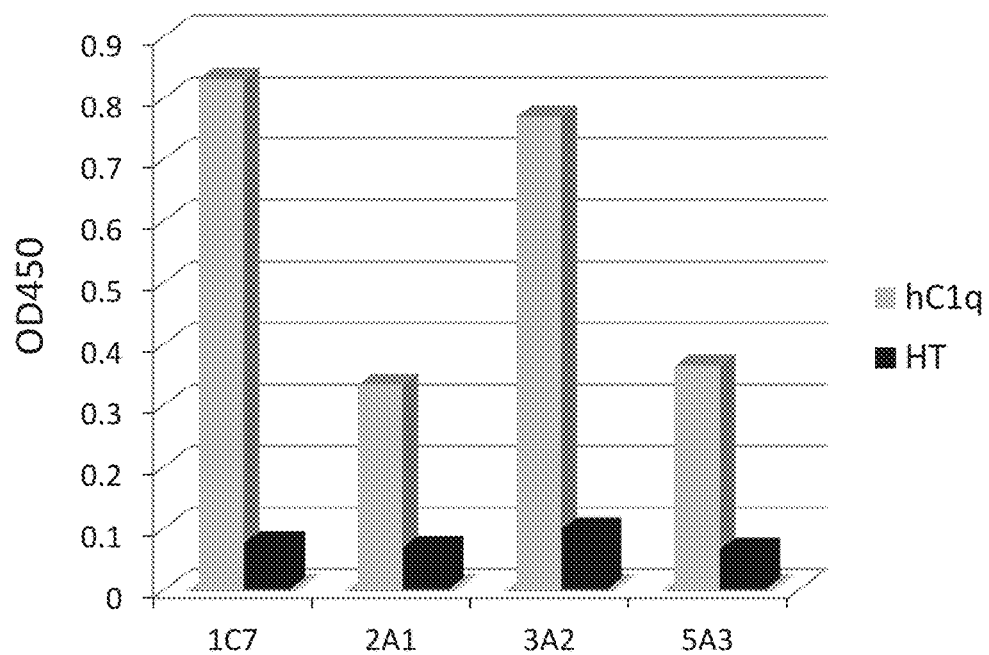
FIG. 1 illustrates the results of an ELISA screen for antibodies specifically binding human C1q. Hybridoma supernatants containing anti-C1q antibodies 1C7, 2A1, 3A2, or 5A3 respectively were tested. Left columns (grey) represent signals for anti-C1q antibody-binding to human C1q protein. Right columns (black) represent signals for anti-C1q antibody-binding to human transferrin (HT).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the anti-C1q antibody to elicit a desired response in the individual. A therapeutically effective amount is also one in which any toxic or detrimental effects of the anti-C1q antibody are outweighed by the therapeutically beneficial effects.

Chronic" administration refers to administration of the medicament(s) in a continuous as opposed to acute mode, so as to maintain the initial therapeutic effect (activity) for an extended period of time. "Intermittent" administration refers to treatment that is not consecutively done without interruption, but rather is cyclic in nature.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, "autoantibody" means any antibody that recognizes a host antigen.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-C1q antibody of the present disclosure, is one that has been identified, separated and/or recovered from a component of its production environment (e.g., naturally or recombinantly). In some embodiments, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody, such as an anti-C1q antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-C1q antibodies of the present disclosure. The V domain mediates antigen binding and defines the specificity of a particular antibody for its particular antigen. However, the variability is not evenly distributed across the entire span of the variable domains.

Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-C1q antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as and anti-C1q antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-C1q antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the $V_H$ and $V_L$ domains which enables the sFv to form the desired structure for antigen binding. For a review of the sFv, see Plückthun in *The*

Pharmacology of Monoclonal Antibodies, vol. 113, Rosenburg and Moore eds., Springer-Verlag, New York, pp. 269-315 (1994).

"Functional fragments" of antibodies, such as anti-C1q antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Nat'l Acad. Sci. USA 90:6444-48 (1993).

As used herein, a "chimeric antibody" refers to an antibody (immunoglobulin), such as an anti-C1q antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Nat'l Acad. Sci. USA, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-C1q antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one that possesses an amino-acid sequence corresponding to that of an antibody, such as an anti-C1q antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol. 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Nat'l Acad. Sci. USA, 103:3557-3562 (2006) regarding human antibodies generated via a human B-cell hybridoma technology.

The term "hypervariable region," "HVR," or "HV," when used herein refers to the regions of an antibody-variable domain, such as that of an anti-C1q antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu in Methods in Molecular Biology 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. In some embodiments, where pre-existing amino acid changes are present in a VH, those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-C1q antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. In some embodiments, the amino acid modification herein is a substitution.

An "affinity-matured" antibody, such as an anti-C1q antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

As use herein, the term "specifically recognizes" or "specifically binds" refers to measurable and reproducible interactions such as attraction or binding between a target and an antibody, such as an anti-C1q antibody of the present disclosure, that is determinative of the presence of the target in the presence of a heterogeneous population of molecules including biological molecules. For example, an antibody, such as an anti-C1q antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a complement protein, such as complement factor C1q, and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

A "blocking" antibody, an "antagonist" antibody, an "inhibitory" antibody, or a "neutralizing" antibody is an antibody, such as an anti-C1q antibody of the present disclosure that inhibits or reduces one or more biological activities of the antigen it binds, such as interactions with one or more proteins. In some embodiments, blocking antibodies, antagonist antibodies, inhibitory antibodies, or "neutralizing" antibodies substantially or completely inhibit one or more biological activities or interactions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, the variant Fc region differs in one or more amino acid substitution(s). In some embodiments, the variant Fc region has at least one amino acid substitution compared to a native sequence Fc region or to the Fc region of a parent polypeptide, e.g. from about one to about ten amino acid substitutions, and, in some embodiments, from about one to about five amino acid substitutions in a native sequence Fc region or in the Fc region of the parent polypeptide. The variant Fc region herein will, in some embodiments, possess at least about 80% homology with a native sequence Fc region and/or with an Fc region of a parent polypeptide, and, in some embodiments, at least about 90% homology therewith, and, in some embodiments, at least about 95% homology therewith.

"Fc receptor" or "FcR" describes a receptor that binds to the Fc region of an antibody. In some embodiments, the FcR is a native sequence human FcR. Moreover, in some embodiments, a FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" molecule or cell is a molecule or a cell that is identified and separated from at least one contaminant molecule or cell with which it is ordinarily associated in the environment in which it was produced. In some embodiments, the isolated molecule or cell is free of association with all components associated with the production environment. The isolated molecule or cell is in a form other than in the form or setting in which it is found in nature. Isolated molecules therefore are distinguished from molecules existing naturally in cells; isolated cells are distinguished from cells existing naturally in tissues, organs, or individuals. In some embodiments, the isolated molecule is an anti-C1q antibody of the present disclosure. In other embodiments, the isolated cell is a host cell or hybridoma cell producing an anti-C1q antibody of the present disclosure.

An "isolated" nucleic acid molecule encoding an antibody, such as an anti-C1q antibody of the present disclosure, is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the invention described herein include "comprising," "consisting," and "consisting essentially of" aspects and embodiments.

Overview

The present disclosure provides anti-C1q antibodies and uses thereof. The anti-C1q antibodies of this disclosure specifically bind a C1q protein of this disclosure. In some embodiments, the anti-C1q antibodies are C1q neutralizing antibodies. In some embodiments, the anti-C1q antibodies of this disclosure may bind to C1 complex.

In certain aspects, the present disclosure provides murine monoclonal antibody M1, which is produced by a hybridoma cell line referred to as mouse hybridoma C1q-M1 7788-1(M) 051613 and which was deposited with ATCC on Jun. 6, 2013 with ATCC Accession Number PTA-120399.

In certain aspects, the present disclosure provides an anti-C1q antibody comprising a light chain variable domain and a heavy chain variable domain, wherein the light chain variable domain comprises the light chain variable domain sequence of antibody M1; and/or wherein the heavy chain comprises the heavy chain variable domain sequence of antibody M1.

In certain aspects, the present disclosure provides an anti-C1q antibody comprising a light chain variable domain and a heavy chain variable domain, wherein the light chain variable domain comprises the HVR-L1, HVR-L2, and HVR-L3 of monoclonal antibody M1 produced by a hybridoma cell line deposited at ATCC with ATCC Accession Number PTA-120399 or progeny thereof and/or wherein the heavy chain variable domain comprises the HVR-H1, HVR-H2, and HVR-H3 of monoclonal antibody M1 produced by a hybridoma cell line deposited at ATCC with Accession Number PTA-120399 or progeny thereof.

In certain aspects, the present disclosure provides an anti-C1q antibody, which binds essentially the same C1q epitope as (1) antibody M1 produced by the hybridoma cell line deposited with ATCC on Jun. 6, 2013 and having ATCC Accession Number PTA-120399 or progeny thereof, (2) an antigen binding fragment of antibody M1, or (3) an antibody comprising the HVR-L1, HVR-L2, HVR-L3, HVR-H1, HVR-H2, and HVR-H3 of antibody M1.

In some embodiments, the anti-C1q antibodies of this disclosure neutralize a biological activity of C1q. Uses for anti-C1q antibodies include, without limitation, the detection of complement factor C1q, e.g., in individuals having a neurodegenerative disorder associated with complement factor 1 (CF1)-dependent pathological synapse loss. Additional non-limiting uses include the inhibition of the classical pathway of complement activation, e.g., in cases where the classical complement pathway is activated by autoantibodies, such as NMO-specific autoantibodies. Further non-limiting uses for anti-C1q antibodies include the diagnosis and treatment of disorders that are associated with elevated expression of complement factors, such as C1q, or associated with the activation of the complement pathway. Such disorders may include, without limitation, autoimmune disorders, inflammatory disorders, and neurodegenerative disorders, including neurodegenerative disorders associated with synapse loss.

In another aspect, the present disclosure provides an isolated nucleic acid molecule encoding an antibody of this disclosure.

The present disclosure also provides isolated host cells containing a nucleic acid molecule that encodes an antibody of this disclosure. In some embodiments, an isolated host cell line is provided that produces the neutralizing monoclonal murine antibody M1. This isolated host cell lines was deposited with ATCC and has ATCC Accession Number PTA-120399.

Additionally, pharmaceutical compositions are provided containing anti-C1q antibodies, such as C1q neutralizing antibodies of this disclosure, in combination with pharmaceutically acceptable carriers. The present disclosure also provides a kit containing an anti-C1q antibody for use in any of the methods described herein.

The present disclosure further provides methods of using the C1q antibodies of this disclosure (e.g., C1q neutralizing antibodies of this disclosure) to treat or prevent a neurodegenerative disease or autoimmune disease in an individual in need of such treatment, to detect synapses in an individual having a neurodegenerative disease or autoimmune disease, and to detect synapses in a biological sample. The present disclosure also provides kits containing the C1q antibodies of this disclosure (e.g., C1q neutralizing antibodies of this disclosure).

Complement Proteins

The antibodies of this disclosure specifically recognize complement factor C1q and/or C1q in the C1 complex of the classical complement activation pathway. The recognized complement factor may be derived, without limitation, from any organism having a complement system, including any mammalian organism such as human, mouse, rat, rabbit, monkey, dog, cat, cow, horse, camel, sheep, goat, or pig.

As used herein "C1 complex" refers to a protein complex that may include, without limitation, one C1q protein, two C1r proteins, and two C1s proteins (e.g., C1qr$^2$s$^2$).

As used herein "complement factor C1q" refers to both wild type sequences and naturally occurring variant sequences.

A non-limiting example of a complement factor C1q recognized by antibodies of this invention is human C1q, including the three polypeptide chains A, B, and C:

C1q, chain A (*homo sapiens*), Accession No. Protein Data Base: NP_057075.1; GenBank No.: NM_015991:

>gi|7705753|ref|NP_057075.1| complement C1q subcomponent subunit A precursor [*Homo sapiens*]

(SEQ ID NO: 1)
MEGPRGWLVLCVLAISLASMVTEDLCRAPDGKKGEAGRPGRRGRPGLKGE

QGEPGAPGIRTGIQGLKGDQGEPGPSGNPGKVGYPGPSGPLGARGIPGIK

GTKGSPGNIKDQPRPAFSAIRRNPPMGGNVVIFDTVITNQEEPYQNHSGR

FVCTVPGYYYFTFQVLSQWEICLSIVSSSRGQVRRSLGFCDTTNKGLFQV

VSGGMVLQLQQGDQVWVEKDPKKGHIYQGSEADSVFSGFLIFPSA

C1q, chain B (*homo sapiens*), Accession No. Protein Data Base: NP_000482.3; GenBank No.: NM_000491.3:
>gi|87298828|ref|NP_000482.3| complement C1q subcomponent subunit B precursor [*Homo sapiens*]

(SEQ ID NO: 2)
MMMKIPWGSIPVLMLLLLLGLIDISQAQLSCTGPPAIPGIPGIPGTPGPD

GQPGTPGIKGEKGLPGLAGDHGEFGEKGDPGIPGNPGKVGPKGPMGPKGG

PGAPGAPGPKGESGDYKATQKIAFSATRTINVPLRRDQTIRFDHVITNMN

NNYEPRSGKFTCKVPGLYYFTYHASSRGNLCVNLMRGRERAQKVVTFCDY

AYNTFQVTTGGMVLKLEQGENVFLQATDKNSLLGMEGANSIFSGFLLFPD

MEA

C1q, chain C (*homo sapiens*), Accession No. Protein Data Base: NP_001107573.1; GenBank No.: NM_001114101.1:
>gi||66235903|ref|NP_001107573.1| complement C1q subcomponent subunit C precursor [*Homo sapiens*]

(SEQ ID NO: 3)
MDVGPSSLPHLGLKLLLLLLLLPLRGQANTGCYGIPGMPGLPGAPGKDGY

DGLPGPKGEPGIPAIPGIRGPKGQKGEPGLPGHPGKNGPMGPPGMPGVPG

PMGIPGEPGEEGRYKQKFQSVFTVTRQTHQPPAPNSLIRFNAVLTNPQGD

YDTSTGKFTCKVPGLYYFVYHASHTANLCVLLYRSGVKVVTFCGHTSKTN

QVNSGGVLLRLQVGEEVWLAVNDYYDMVGIQGSDSVFSGFLLFPD

Accordingly, an anti-C1q antibody of the present disclosure may bind to polypeptide chain A, polypeptide chain B, and/or polypeptide chain C of a C1q protein. In some embodiments, an anti-C1q antibody of the present disclosure binds to polypeptide chain A, polypeptide chain B, and/or polypeptide chain C of human C1q or a homolog thereof, such as mouse, rat, rabbit, monkey, dog, cat, cow, horse, camel, sheep, goat, or pig C1q.

Anti-C1q Antibodies

The antibodies of this disclosure specifically bind to a complement factor C1q and/or C1q in the C1 complex of the classical complement pathway. In some embodiments, the anti-C1q antibodies specifically bind to human C1q. In some embodiments, the anti-C1q antibodies specifically bind to human and mouse C1q. In some embodiments, the anti-C1q antibodies specifically bind to rat C1q. In some embodiments, the anti-C1q antibodies specifically bind to human C1q, mouse C1q, and rat C1q.

In some embodiments, the anti-C1q antibodies of this disclosure neutralize a biological activity of complement factor C1q. In some embodiments, the antibodies inhibit the interaction between complement factor C1q and other complement factors, such as C1r or C1s or between C1q and an antibody, such as an autoantibody. As disclosed herein, an autoantibody of the present disclosure includes, without limitation, an antibody that recognizes a host antigen and activates the classical pathway of complement activation. In the first step of this activation process complement factor C1q binds to the autoantibody-autoantigen-immune complex. In some embodiments, the antibodies inhibit the interaction between complement factor C1q and a non-complement factor. A non-complement factor may include phosphatidylserine, pentraxin-3, C-reactive protein (CRP), globular C1q receptor (gC1qR), complement receptor 1 (CR1), β-amyloid, and calreticulin. In some embodiments, the antibodies inhibit the classical complement activation pathway. In certain embodiments, the antibodies further inhibit the alternative pathway. In some embodiments, the antibodies inhibit autoantibody- and complement-dependent cytotoxicity (CDC). In some embodiments, the antibodies inhibit complement-dependent cell-mediated cytotoxicity (CDCC). In some embodiments, the antibodies inhibit B-cell antibody production, dendritic cell maturation, T-cell proliferation, cytokine production, or microglia activation. In some embodiments, the antibodies inhibit the Arthus reaction. In some embodiments, the antibodies inhibit phagocytosis of synapses or nerve endings. In some embodiments, the antibodies inhibit the activation of complement receptor 3 (CR3/C3) expressing cells.

The functional properties of the antibodies of this invention, such as dissociation constants for antigens, inhibition of protein-protein interactions (e.g., C1q-autoantibody interactions), inhibition of autoantibody-dependent and complement-dependent cytotoxicity (CDC), inhibition of complement-dependent cell-mediated cytotoxicity (CDCC), or lesion formation, may, without limitation, be measured in in vitro, ex vivo, or in vivo experiments.

The dissociation constants ($K_D$) of the anti-C1q antibodies for C1q may be less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.5 nM, less than 0.1 nM, less than 0.05 nM, less than 0.01 nM, or less than 0.005 nM. In some embodiments, dissociation constants range from less than about 30 nM to less than about 100 pM. In some embodiments, dissociation constants are less than about 30 nM. In some embodiments, dissociation constants are less than about 20 nM. In some embodiments, dissociation constants are less than about 10 nM. In some embodiments, dissociation constants are less than about 5 nM. In some embodiments, dissociation constants are less than about 1 nM. In some embodiments, dissociation constants are less than about 100 pM. In certain embodiments, the dissociation constants of the anti-C1q antibody range from less than about 30 nM to less than about 100 pM for human C1q, and range from less than about 30 nM to less than about 100 pM for mouse C1q. In certain embodiments, dissociation constants of the anti-C1q antibody are less than about 30 nM for human C1q and less than about 30 nM for mouse C1q. In certain embodiments, dissociation constants of the anti-C1q antibody are less than about 20 nM for human C1q and less than about 20 nM for mouse C1q. In certain embodiments, dissociation constants of the anti-C1q antibody are less than about 10 nM for human C1q and less than about 10 nM for mouse C1q. In certain embodiments, dissociation constants of the anti-C1q antibody are less than about 5 nM for human C1q and less than about 5 nM for mouse C1q. In certain embodiments, dissociation constants of the anti-C1q antibody are less than about 1 nM for human C1q and less than about 1 nM mouse C1q. In certain embodiments, the dissociation constants of the anti-C1q antibody are less than 100 pM for human C1q and less than 100 pM for mouse C1q. Antibody dissociation constants for antigens other than C1q may be least 5-fold, at least 10-fold, at least 100-fold, at least 1,000-fold, at least 10,000-fold, or at least 100,000-fold higher that the dissociation constants for C1q. For example, the dissociation constant of a C1q antibody of this disclosure may be at least 1,000-fold higher for C1s than for C1q. Dissociation constants may be determined through any analytical technique, including any biochemical or biophysical technique such as ELISA, surface plasmon resonance (SPR), bio layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. Dissociation constants ($K_D$) of the anti-C1q antibodies for C1q may be determined, e.g., using full-length antibodies or antibody fragments, such as Fab fragments.

One exemplary way of determining binding affinity of antibodies to C1q is by measuring binding affinity of monofunctional Fab fragments of the antibody. To obtain monofunctional Fab fragments, an antibody (for example, IgG) can be cleaved with papain or expressed recombinantly. The affinity of an Fab fragment of an antibody can be determined by surface plasmon resonance (Biacore3000™ surface plasmon resonance (SPR) system, Biacore™, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human C1q (or any other C1q) can be diluted into HBS-EP buffer to a concentration of less than 0.5 µg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of C1q on the chip for over 200 injections. Typically, serial dilutions (spanning concentrations of 0.1-10.times. estimated $K_D$) of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any C1q, including human C1q, C1q of another mammal (such as mouse C1q, rat C1q, primate C1q), as well as different forms of C1q. Binding affinity of an antibody is generally measured at 25° C., but can also be measured at 37° C.

The antibodies of this disclosure may bind to C1q antigens derived from any organism having a complement system, including any mammalian organism such as human, mouse, rat, rabbit, monkey, dog, cat, cow, horse, camel, sheep, goat, or pig. In some embodiments, the anti-C1q antibodies bind specifically to epitopes on human C1q. In some embodiments, the anti-C1q antibodies specifically bind to epitopes on both human and mouse C1q. In some embodiments, the anti-C1q antibodies specifically bind to epitopes on human, mouse, and rat C1q.

In some embodiments, provided herein is an anti-C1q antibody that binds to an epitope of C1q that is the same as or overlaps with the C1q epitope bound by another antibody of this disclosure. In certain embodiments, provided herein is an anti-C1q antibody that binds to an epitope of C1q that is the same as or overlaps with the C1q epitope bound by anti-C1q antibody M1. In some embodiments, the anti-C1q antibody competes with another antibody of this disclosure for binding to C1q. In certain embodiments, the anti-C1q antibody competes with anti-C1q antibody M1 or an antigen-binding fragment thereof for binding to C1q.

Methods that may be used to determine which C1q epitope of an anti-C1q antibody binds to, or whether two antibodies bind to the same or an overlapping epitope, may include, without limitation, X-ray crystallography, NMR spectroscopy, Alanine-Scanning Mutagenesis, the screening of peptide libraries that include C1q-derived peptides with overlapping C1q sequences, and competition assays. Competition assays are especially useful to determine whether two antibodies bind the same epitope by recognizing identical or sterically overlapping epitopes or whether one antibody competitively inhibits binding of another antibody to the antigen. These assays are known in the art. Typically, an antigen or antigen expressing cells are immobilized on a multi-well plate and the ability of unlabeled antibodies to block the binding of labeled antibodies is measured. Common labels for such competition assays are radioactive labels or enzyme labels.

Competitive antibodies encompassed herein are antibodies that inhibit (i.e., prevent or interfere with in comparison to a control) or reduce the binding of any anti-C1q antibody of this disclosure (such as M1 or an antigen-binding fragment of M1) to C1q by at least 50%, 60%, 70%, 80%, 90% and 95% at 1 µM or less. For example, the concentration competing antibody in the competition assay may be at or below the $K_D$ of antibody M1 or an antigen-binding fragment of M1. Competition between binding members may be readily assayed in vitro for example using ELISA and/or by monitoring the interaction of the antibodies with C1q in solution. The exact means for conducting the analysis is not critical. C1q may be immobilized to a 96-well plate or may be placed in a homogenous solution. In specific embodiments, the ability of unlabeled candidate antibody(ies) to block the binding of the labeled anti-C1q antibody, e.g. M1, can be measured using radioactive, enzyme or other labels. In the reverse assay, the ability of unlabeled antibodies to interfere with the interaction of a labeled anti-C1q antibody with C1q wherein said labeled anti-C1q antibody, e.g., M1, and C1q are already bound is determined. The readout is through measurement of bound label. C1q and the candidate antibody(ies) may be added in any order or at the same time.

In some embodiments, the anti-C1q antibody inhibits the interaction between C1q and an autoantibody. In some embodiments, the anti-C1q antibody is murine anti-human C1q monoclonal antibody M1, which is produced by a hybridoma cell line deposited with ATCC on Jun. 6, 2013 with ATCC Accession Number PTA-120399.

In some embodiments, the anti-C1q antibody is an isolated antibody which binds essentially the same C1q epitope as M1. In some embodiments, the anti-C1q antibody is an isolated antibody comprising the HVR-L1, HVR-L2, and HVR-L3 of the light chain variable domains of monoclonal antibody M1 produced by the hybridoma cell line deposited with ATCC on Jun. 6, 2013 with ATCC Accession Number PTA-120399, or progeny thereof. In some embodiments, the anti-C1q antibody is an isolated antibody comprising the HVR-H1, HVR-H2, and HVR-H3 of the heavy chain variable domains of monoclonal antibody M1 produced by the hybridoma cell line deposited with ATCC on Jun. 6, 2013 with ATCC Accession Number PTA-120399, or progeny thereof. In some embodiments, the anti-C1q antibody is an isolated antibody comprising the HVR-L1, HVR-L2, and HVR-L3 of the light chain variable domains and the HVR-H1, HVR-H2, and HVR-H3 of the heavy chain variable domains of monoclonal antibody M1 produced by the hybridoma cell line deposited with ATCC on Jun. 6, 2013 with ATCC Accession Number PTA-120399, or progeny thereof.

In some embodiments, the anti-C1q antibody binds to a C1q protein and binds to one or more amino acids of the C1q protein within amino acid residues selected from (a) amino acid residues 196-226 of SEQ ID NO:1 (SEQ ID NO:16), or amino acid residues of a C1q protein chain A (C1qA) corresponding to amino acid residues 196-226 (GLFQVVSGGMVLQLQQGDQVWVEKDPKKGHI) of SEQ ID NO:1 (SEQ ID NO:16); (b) amino acid residues 196-221 of SEQ ID NO:1 (SEQ ID NO:17), or amino acid residues of a C1qA corresponding to amino acid residues 196-221 (GLFQVVSGGMVLQLQQGDQVWVEKDP) of SEQ ID. NO:1 (SEQ ID NO:17); (c) amino acid residues 202-221 of SEQ ID NO:1 (SEQ ID NO:18), or amino acid residues of a C1qA corresponding to amino acid residues 202-221 (SGGMVLQLQQGDQVWVEKDP) of SEQ ID NO:1 (SEQ ID NO:18); (d) amino acid residues 202-219 of SEQ ID NO:1 (SEQ ID NO:19), or amino acid residues of a C1qA corresponding to amino acid residues 202-219 (SGGMVLQLQQGDQVWVEK) of SEQ ID NO:1 (SEQ ID NO:19); and (e) amino acid residues Lys 219 and/or Ser 202 of SEQ ID NO:1, or amino acid residues of a C1qA corresponding Lys 219 and/or Ser 202 of SEQ ID NO:1.

In some embodiments, the antibody further binds to one or more amino acids of the C1q protein within amino acid residues selected from: (a) amino acid residues 218-240 of SEQ ID NO:3 (SEQ ID NO:20) or amino acid residues of a C1q protein chain C (C1qC) corresponding to amino acid residues 218-240 (WLAVNDYYDMVGI QGSDSVFSGF) of SEQ ID NO:3 (SEQ ID NO:20); (b) amino acid residues 225-240 of SEQ ID NO:3 (SEQ ID NO:21) or amino acid residues of a C1qC corresponding to amino acid residues 225-240 (YDMVGI QGSDSVFSGF) of SEQ ID NO:3 (SEQ ID NO:21); (c) amino acid residues 225-232 of SEQ ID NO:3 (SEQ ID NO:22) or amino acid residues of a C1qC corresponding to amino acid residues 225-232 (YDMVGIQG) of SEQ ID NO:3 (SEQ ID NO:22); (d) amino acid residue Tyr 225 of SEQ ID NO:3 or an amino acid residue of a C1qC corresponding to amino acid residue Tyr 225 of SEQ ID NO:3; (e) amino acid residues 174-196 of SEQ ID NO:3 (SEQ ID NO:23) or amino acid residues of a C1qC corresponding to amino acid residues 174-196 (HTANLCVLLYRSGVKVVTFCGHT) of SEQ ID NO:3 (SEQ ID NO:23); (f) amino acid residues 184-192 of SEQ ID NO:3 (SEQ ID NO:24) or amino acid residues of a C1qC corresponding to amino acid residues 184-192 (RSGVKVVTF) of SEQ ID NO:3 (SEQ ID NO:24); (g) amino acid residues 185-187 of SEQ ID NO:3 or amino acid residues of a C1qC corresponding to amino acid residues 185-187 (SGV) of SEQ ID NO:3; (h) amino acid residue Ser 185 of SEQ ID NO:3 or an amino acid residue of a C1qC corresponding to amino acid residue Ser 185 of SEQ ID NO:3.

In certain embodiments, the anti-C1q antibody binds to amino acid residue Lys 219 and Ser 202 of the human C1qA as shown in SEQ ID NO:1 or amino acids of a human C1qA corresponding to Lys 219 and Ser 202 as shown in SEQ ID NO:1, and amino acid residue Tyr 225 of the human C1qC as shown in SEQ ID NO:3 or an amino acid residue of a human C1qC corresponding to Tyr 225 as shown in SEQ ID NO:3. In certain embodiments, the anti-C1q antibody binds to amino acid residue Lys 219 of the human C1qA as shown in SEQ ID NO:1 or an amino acid residue of a human C1qA corresponding to Lys 219 as shown in SEQ ID NO:1, and amino acid residue Ser 185 of the human C1qC as shown in SEQ ID NO:3 or an amino acid residue of a human C1qC corresponding to Ser 185 as shown in SEQ ID NO:3.

In some embodiments, the anti-C1q antibody binds to a C1q protein and binds to one or more amino acids of the C1q protein within amino acid residues selected from: (a) amino acid residues 218-240 of SEQ ID NO:3 (SEQ ID NO:20) or amino acid residues of a C1qC corresponding to amino acid residues 218-240 (WLAVNDYYDMVGI QGSDSVFSGF) of SEQ ID NO:3 (SEQ ID NO:20); (b) amino acid residues 225-240 of SEQ ID NO:3 (SEQ ID NO:21) or amino acid residues of a C1qC corresponding to amino acid residues 225-240 (YDMVGI QGSDSVFSGF) of SEQ ID NO:3 (SEQ ID NO:21); (c) amino acid residues 225-232 of SEQ ID NO:3 (SEQ ID NO:22) or amino acid residues of a C1qC corresponding to amino acid residues 225-232 (YDMVGIQG) of SEQ ID NO:3 (SEQ ID NO:22); (d) amino acid residue Tyr 225 of SEQ ID NO:3 or an amino acid residue of a C1qC corresponding to amino acid residue Tyr 225 of SEQ ID NO:3; (e) amino acid residues 174-196 of SEQ ID NO:3 (SEQ ID NO:23) or amino acid residues of a C1qC corresponding to amino acid residues 174-196 (HTANLCVLLYRSGVKVVTFCGHT) of SEQ ID NO:3 (SEQ ID NO:23); (f) amino acid residues 184-192 of SEQ ID NO:3 (SEQ ID NO:24) or amino acid residues of a C1qC corresponding to amino acid residues 184-192 (RSGVKVVTF) of SEQ ID NO:3 (SEQ ID NO:24); (g) amino acid residues 185-187 of SEQ ID NO:3 or amino acid residues of a C1qC corresponding to amino acid residues 185-187 (SGV) of SEQ ID NO:3; (h) amino acid residue Ser 185 of SEQ ID NO:3 or an amino acid residue of a C1qC corresponding to amino acid residue Ser 185 of SEQ ID NO:3.

In some embodiments, the anti-C1q antibody of this disclosure inhibits the interaction between C1q and C1s. In some embodiments, the anti-C1q antibody inhibits the interaction between C1q and C1r. In some embodiments the anti-C1q antibody inhibits the interaction between C1q and C1s and between C1q and C1r. In some embodiments, the anti-C1q antibody inhibits the interaction between C1q and another antibody, such as an autoantibody. In some embodiments, the anti-C1q antibody inhibits the respective interactions, at a stoichiometry of less than 2.5:1; 2.0:1; 1.5:1; or 1.0:1. In some embodiments, the C1q antibody inhibits an interaction, such as the C1q-C1s interaction, at approximately equimolar concentrations of C1q and the anti-C1q antibody. In other embodiments, the anti-C1q antibody binds to C1q with a stoichiometry of less than 20:1; less than 19.5:1; less than 19:1; less than 18.5:1; less than 18:1; less than 17.5:1; less than 17:1; less than 16.5:1; less than 16:1; less than 15.5:1; less than 15:1; less than 14.5:1; less than 14:1; less than 13.5:1; less than 13:1; less than 12.5:1; less than 12:1; less than 11.5:1; less than 11:1; less than 10.5:1; less than 10:1; less than 9.5:1; less than 9:1; less than 8.5:1; less than 8:1; less than 7.5:1; less than 7:1; less than 6.5:1; less than 6:1; less than 5.5:1; less than 5:1; less than 4.5:1; less than 4:1; less than 3.5:1; less than 3:1; less than 2.5:1; less than 2.0:1; less than 1.5:1; or less than 1.0:1. In certain embodiments, the anti-C1q antibody binds C1q with a binding stoichiometry that ranges from 20:1 to 1.0:1 or less than 1.0:1. In certain embodiments, the anti-C1q antibody binds C1q with a binding stoichiometry that ranges from 6:1 to 1.0:1 or less than 1.0:1. In certain embodiments, the anti-C1q antibody binds C1q with a binding stoichiometry that ranges from 2.5:1 to 1.0:1 or less than 1.0:1. In some embodiments, the anti-C1q antibody inhibits the interaction between C1q and C1r, or between C1q and C1s, or between C1q and both C1r and C1s. In some embodiments, the anti-C1q antibody inhibits the interaction between C1q and C1r, between C1q and C1s, and/or between C1q and both C1r and C1s. In some embodiments, the anti-C1q antibody binds to the C1q A-chain. In other embodiments, the anti-C1q antibody binds to the C1q B-chain. In other embodiments, the anti-C1q antibody binds to the C1q C-chain. In some embodiments, the anti-C1q antibody binds to the C1q A-chain, the C1q B-chain and/or the C1q C-chain. In some embodiments, the anti-C1q antibody binds to the globular domain of the C1q A-chain, B-chain, and/or C-chain. In other embodiments, the anti-C1q antibody binds to the collagen-like domain of the C1q A-chain, the C1q B-chain, and/or the C1q C-chain.

Where antibodies of this disclosure inhibit the interaction between two or more complement factors, such as the interaction of C1q and C1s, or the interaction between C1q and C1r, the interaction occurring in the presence of the antibody may be reduced by at least 10%, at least 20%, at least 30%, at least 40%, at least 50%, at least 60%, at least 70%, at least 80%, at least 90%, at least 95%, or at least 99% relative to a control wherein the antibodies of this disclosure are absent. In certain embodiments, the interaction occurring in the presence of the antibody is reduced by an amount that ranges from at least 30% to at least 99% relative to a control wherein the antibodies of this disclosure are absent.

In some embodiments, the antibodies of this disclosure inhibit C4-cleavage by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. Methods for measuring C4-cleavage are well known in the art. The $EC_{50}$ values for antibodies of this disclosure with respect C4-cleavage may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In some embodiments, the antibodies of this disclosure inhibit C4-cleavage at approximately equimolar concentrations of C1q and the respective anti-C1q antibody.

In some embodiments, the antibodies of this disclosure inhibit autoantibody-dependent and complement-dependent cytotoxicity (CDC) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. The $EC_{50}$ values for antibodies of this disclosure with respect to inhibition of autoantibody-dependent and complement-dependent cytotoxicity may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml.

In some embodiments, the antibodies of this disclosure inhibit complement-dependent cell-mediated cytotoxicity (CDCC) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. Methods for measuring CDCC are well known in the art. The $EC_{50}$ values for antibodies of this disclosure with respect CDCC inhibition may be 1 less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In some embodiments, the antibodies of this disclosure inhibit CDCC but not antibody-dependent cellular cytotoxicity (ADCC).

In some embodiments, the antibodies of this disclosure inhibit C1F hemolysis (also referred to as CH50 hemolysis) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent or wherein control antibodies are used that do not bind to a complement factor or another antibody such as an autoantibody (see, e.g., Example 3). Methods for measuring C1F hemolysis are well known in the art (see, e.g., Example 3). The $EC_{50}$ values for antibodies of this disclosure with respect to C1F hemolysis may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In some embodiments, the anti-C1q antibodies of this disclosure neutralize at least 50% of C1F hemolysis at a dose of less than 200 ng/ml, less than 100 ng/ml, less than 50 ng/ml, or less than 20 ng/ml. In some embodiments, the antibodies of this disclosure neutralize C1F hemolysis at approximately equimolar concentrations of C1q and the anti-C1q antibody. In some embodiments, the anti-C1q antibodies of this disclosure neutralize hemolysis in a human C1F hemolysis assay. In some embodiments, the antibodies of this disclosure neutralize hemolysis in a human, mouse, and rat C1F hemolysis assay (see, e.g., Example 3).

In some embodiments, the alternative pathway may amplify CDC initiated by C1q binding and subsequent C1s activation; in at least some of these embodiments, the antibodies of this disclosure inhibit the alternative pathway by at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure were absent.

In some embodiments, the antibodies of this disclosure prevent synaptic loss in a cellular in vitro model or an in vivo model of synaptic loss, such as an in vivo mouse model. In vivo mouse models may include Tg2576, a mouse amyloid precursor protein (APP) transgenic model of Alzheimer's disease, R6/2 NT-CAG150, a transgenic model for Huntington's disease, or SMAΔ7, a mouse model for Spinal Muscular Atrophy, or DBA/2J, a genetic mouse model of glaucoma. In general, any neurodegenerative disease model may be used that displays synapse loss.

Methods for measuring synaptic loss in vitro or in vivo are well known in the art. In vitro lesion formation may be reduced by at least 30%, at least 40%, at least 50%, at least 60%, at least 70%, at least 80%, at least 90%, or at least 95%, or by an amount that ranges from at least 30% to at least 95%, relative to a control experiment in which antibodies of this disclosure are absent. The $EC_{50}$ values for antibodies of this disclosure with respect to the prevention of in vitro lesion formation may be less than 3 µg/ml; 2.5 µg/ml; 2.0 µg/ml; 1.5 µg/ml; 1.0 µg/ml; 0.5 µg/ml; 0.25 µg/ml; 0.1 µg/ml; 0.05 µg/ml. In vivo synaptic loss may be reduced by at least 5%, at least 10%, at least 15%, at least 20%, at least 35%, at least 40%, or at least 50%, or by an amount that ranges from at least 5% to at least 50%, relative to a control experiment in which antibodies of this disclosure are absent.

In some embodiments, the antibodies of this disclosure prevent lesion formation in an ex vivo spinal cord slice model of NMO or in an in vivo mouse model of NMO. Methods for measuring lesion formation ex vivo or in vivo are well known in the art. Ex vivo lesion formation may be reduced at least by a relative score of 0.5, 1.0, 1.5, 2.0, 2.5, 3.0, 3.5, or 4.0. The $EC_{50}$ values for antibodies of this disclosure with respect to the prevention of ex vivo lesion formation may be less than 3 µg/ml; less than 2.5 µg/ml; less than 2.0 µg/ml; less than 1.5 µg/ml; less than 1.0 µg/ml; less than 0.5 µg/ml; less than 0.25 µg/ml; less than 0.1 µg/ml; or less than 0.05 µg/ml. In vivo lesion formation may be reduced by at least 5%, at least 10%, at least 15%, at least 20%, at least 35%, at least 40%, or at least 50%, or by an amount that ranges from at least 5% to at least 50%, in terms of loss of staining (% of area). Staining may be assessed, without limitation, by APQ4 staining, GFAP staining, or MBP staining.

The present disclosure provides anti-C1q antibodies. The antibodies of this disclosure may have one or more of the following characteristics. The antibodies of this disclosure may be polyclonal antibodies, monoclonal antibodies, humanized antibodies, human antibodies, antibody fragments, bispecific and polyspecific antibodies, multivalent antibodies, or heteroconjugate antibodies. Antibody fragments of this disclosure may be functional fragments that bind the same epitope as any of the anti-C1q antibodies of this disclosure. In some embodiments, the antibody fragments of this disclosure specifically bind to and neutralize a biological activity of C1q. In some embodiments, the antibody fragments are miniaturized versions of the anti-C1q antibodies or antibody fragments of this disclosure that have the same epitope of the corresponding full-length antibody, but have much smaller molecule weight. Such miniaturized anti-C1q antibody fragments may have better brain penetration ability and a shorter half-life, which is advantageous for imaging and diagnostic utilities (see e.g., Lütje S et al., *Bioconjug Chem.* 2014 Feb. 19; 25(2):335-41; Tavaré R et al., *Proc Natl Acad Sci USA.* 2014 Jan. 21; 111(3):1108-13; and Wiehr S et al., *Prostate.* 2014 May; 74(7):743-55). Accordingly, in some embodiments, anti-C1q antibody fragments of this disclosure have better brain penetration as compared to their corresponding full-length antibodies and/or have a shorter half-life as compared to their corresponding full-length antibodies. In some embodiments, anti-C1q antibodies of the present disclosure are bispecific antibodies recognizing a first antigen and a second antigen. In some embodiments, the first antigen is a C1q antigen. In some embodiments, the second antigen is an antigen facilitating transport across the blood-brain-barrier, including without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005. The antibodies of this disclosure may further contain engineered effector functions, amino acid sequence modifications or other antibody modifications known in the art; e.g., the constant region of the anti-C1q antibodies described herein may be modified to impair complement activation.

Additional anti-C1q antibodies, e.g., antibodies that specifically bind to a C1q protein of the present disclosure, may be identified, screened, and/or characterized for their physical/chemical properties and/or biological activities by various assays known in the art.

Antibody Preparation

Anti-C1q antibodies of the present disclosure can encompass polyclonal antibodies, monoclonal antibodies, humanized antibodies, chimeric antibodies, human antibodies, antibody fragments (e.g., Fab, Fab'-SH, Fv, scFv, and F(ab')$_2$ fragments), bispecific and polyspecific antibodies, multivalent antibodies, heteroconjugate antibodies, library derived antibodies, antibodies having modified effector functions, fusion proteins containing an antibody portion, and any other modified configuration of the immunoglobulin molecule that includes an antigen recognition site, such as an epitope having amino acid residues of a C1q protein of the present disclosure, including glycosylation variants of antibodies, amino acid sequence variants of antibodies, and covalently modified antibodies. The anti-C1q antibodies may be human, murine, rat, or of any other origin (including chimeric or humanized antibodies).

(1) Polyclonal Antibodies

Polyclonal antibodies, such as polyclonal anti-C1q antibodies, are generally raised in animals by multiple subcutaneous (sc) or intraperitoneal (ip) injections of the relevant antigen and an adjuvant. It may be useful to conjugate the relevant antigen (e.g., a purified or recombinant C1q protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 µg (for rabbits) or 5 µg (for mice) of the protein or conjugate with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant-cell culture as protein fusions. Also, aggregating agents such as alum are suitable to enhance the immune response.

(2) Monoclonal Antibodies

Monoclonal antibodies, such as monoclonal anti-C1q antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-C1q antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant C1q protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The immunizing agent will typically include the antigenic protein (e.g., a purified or recombinant C1q protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that may contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells.

In some embodiments, immortalized myeloma cells are those that fuse efficiently, support stable high-level production of antibody by the selected antibody-producing cells, and are sensitive to a medium such as HAT medium. Among these, are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a C1q protein of the present disclosure). In some embodiments, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a C1q protein of the present disclosure). In some embodiments, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-C1q monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a source of such DNA. Once isolated, the DNA may be placed into expression vectors, which are then transfected into host-cells such as *E. coli* cells, simian COS cells, Chinese hamster ovary (CHO) cells, or myeloma cells that do not otherwise produce immunoglobulin protein, in order to synthesize monoclonal antibodies in such recombinant host-cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, anti-C1q antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a C1q protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-C1q antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-C1q antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-C1q antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992). In some embodiments, the anti-C1q antibody is a chimeric antibody comprising the heavy and light chain variable domains of any of the anti-C1q antibody described herein (e.g., antibody M1 and 4A4B11) and constant regions from a human immunoglobulin.

Methods for humanizing non-human anti-C1q antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., C1q proteins of the present disclosure), is achieved. In general, the CDR residues are directly and most substantially involved in influencing antigen binding.

Various forms of the humanized anti-C1q antibody are contemplated. For example, the humanized anti-C1q antibody may be an antibody fragment, such as an Fab, which is optionally conjugated with one or more cytotoxic agent(s) in order to generate an immunoconjugate. Alternatively, the humanized anti-C1q antibody may be an intact antibody, such as an intact IgG1 antibody.

(4) Human Antibodies

Alternatively, human anti-C1q antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region (JO gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Nat'l Acad. Sci. USA*, 90:2551 (1993); Jakobovits et al., *Nature*, 362:255-258 (1993); Bruggermann et al., *Year in Immunol.*, 7:33 (1993); U.S. Pat. No. 5,591,669 and WO 97/17852.

Alternatively, phage display technology can be used to produce human anti-C1q antibodies and antibody fragments in vitro, from immunoglobulin variable (V) domain gene repertoires from unimmunized donors. McCafferty et al., *Nature* 348:552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also U.S. Pat. Nos. 5,565,332 and 5,573,905. Additionally, yeast display technology can be used to produce human anti-C1q antibodies and antibody fragments in vitro (e.g., WO 2009/036379; WO 2010/105256; WO 2012/009568; US 2009/0181855; US 2010/0056386; and Feldhaus and Siegel (2004) J. Immunological Methods 290:69-80). In other embodiments, ribosome display technology can be used to produce human anti-C1q antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Plückthun (2004) J. Immunological Methods 290:51-67).

The techniques of Cole et al., and Boerner et al., are also available for the preparation of human anti-C1q monoclonal antibodies (Cole et al., Monoclonal Antibodies and Cancer Therapy, Alan R. Liss, p. 77 (1985) and Boerner et al., J. Immunol. 147(1): 86-95 (1991). Similarly, human anti-C1q antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., Bio/Technology 10: 779-783 (1992); Lonberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lonberg and Huszar, Intern. Rev. Immunol. 13: 65-93 (1995).

Finally, human anti-C1q antibodies may also be generated in vitro by activated B-cells (see U.S. Pat. Nos. 5,567,610 and 5,229,275).

(5) Antibody Fragments

In certain embodiments there are advantages to using anti-C1q antibody fragments, rather than whole anti-C1q antibodies. Smaller fragment sizes allow for rapid clearance.

Various techniques have been developed for the production of antibody fragments. Traditionally, these fragments were derived via proteolytic digestion of intact antibodies (see, e.g., Morimoto et al., J. Biochem. Biophys. Method. 24:107-117 (1992); and Brennan et al., Science 229:81 (1985)). However, these fragments can now be produced directly by recombinant host-cells, for example, using nucleic acids encoding anti-C1q antibodies of the present disclosure. Fab, Fv and scFv antibody fragments can all be expressed in and secreted from E. coli, thus allowing the straightforward production of large amounts of these fragments. A anti-C1q antibody fragments can also be isolated from the antibody phage libraries as discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host-cell culture. Production of Fab and $F(ab')_2$ antibody fragments with increased in vivo half-lives are described in U.S. Pat. No. 5,869,046. In other embodiments, the antibody of choice is a single chain Fv fragment (scFv). See WO 93/16185; U.S. Pat. No. 5,571,894 and U.S. Pat. No. 5,587,458. The anti-C1q, anti-C1r, or anti-C1q antibody fragment may also be a "linear antibody," e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., one or more C1q proteins of the present disclosure). Alternatively, one part of a BsAb can be armed to bind to the target C1q antigen, and another can be combined with an arm that binds to a second protein. Such antibodies can be derived from full length antibodies or antibody fragments (e.g., $F(ab')_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., Nature, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10:3655-3659 (1991).

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, $C_H2$, and $C_H3$ regions. In some embodiments, the first heavy-chain constant region ($C_H1$) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant-cell culture. The interface may comprise at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and VH domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different antigens. In some embodiments a bispecific antibody binds to a first antigen, C1q, and a second antigen facilitating transport across the blood-brain barrier. Numerous antigens are known in the art that facilitate transport across the blood-brain barrier (see, e.g., Gabathuler R., Approaches to transport therapeutic drugs across the blood-brain barrier to treat brain diseases, Neurobiol. Dis. 37 (2010) 48-57). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, and Angiopep peptides such as ANG1005 (see, e.g., Gabathuler, 2010).

(7) Multivalent Antibodies

A multivalent antibody may be internalized (and/or catabolized) faster than a bivalent antibody by a cell expressing an antigen to which the antibodies bind. The anti-C1q antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In some embodiments, the dimerization domain comprises an Fc region or a hinge region. In this scenario, the antibody will comprise an Fc region and three or more antigen binding sites amino-terminal to the Fc region. In some embodiments, the multivalent antibody herein contains three to about eight, and in some embodiments four, antigen binding sites. The multivalent antibody contains at least one polypeptide chain (and in some embodiments two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein may further comprise at least two (and in some embodiments four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

(8) Heteroconjugate Antibodies

Heteroconjugate antibodies are also within the scope of the present disclosure. Heteroconjugate antibodies are composed of two covalently joined antibodies (e.g., anti-C1q antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(9) Effector Function Engineering

It may also be desirable to modify an anti-C1q antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

The constant region of the anti-complement antibodies described herein may also be modified to impair complement activation. For example, complement activation of IgG antibodies following binding of the C1 component of complement may be reduced by mutating amino acid residues in the constant region in a C1 binding motif (e.g., C1q binding motif). It has been reported that Ala mutation for each of D270, K322, P329, P331 of human IgG1 significantly reduced the ability of the antibody to bind to C1q and activating complement. For murine IgG2b, C1q binding motif constitutes residues E318, K320, and K322. Idusogie et al. (2000) *J. Immunology* 164:4178-4184; Duncan et al. (1988) *Nature* 322: 738-740. As the C1s binding motif E318, K320, and K322 identified for murine IgG2b is believed to be common for other antibody isotypes (Duncan et al. (1988) *Nature* 322:738-740), C1q binding activity for IgG2b can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also possible to use such polar non-ionic residues as Ser, Thr, Cys, and Met in place of residues 320 and 322, but not 318, in order to abolish C1s binding activity. In addition, removal of carbohydrate modifications of the Fc region necessary for complement binding can prevent complement activation Glycosylation of a conserved asparagine (Asn-297) on the CH2 domain of IgG heavy chains is essential for antibody effector functions (Jefferis et al. (1998) Immunol Rev 163:59-76). Modification of the Fc glycan alters IgG conformation and reduces the Fc affinity for binding of complement protein C1q and effector cell receptor FcR (Alhorn et al. (2008) PLos ONE 2008; 3:e1413). Complete removal of the Fc glycan abolishes CDC and ADCC. Deglycosylation can be performed using glycosidase enzymes for example Endoglycosidase S (EndoS), a 108 kDa enzyme encoded by the gene endoS of *Streptococcus pyogenes* that selectively digests asparagine-linked glycans on the heavy chain of all IgG subclasses, without action on other immunoglobulin classes or other glycoproteins (Collin et al. (2001) EMBO J 2001; 20:3046-3055).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(10) Other Amino Acid Sequence Modifications

Amino acid sequence modifications of anti-C1q antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a C1q protein of the present disclosure). The amino acid changes also may alter post-translational processes of the antibody, such as changing the number or position of glycosylation sites.

A useful method for identification of certain residues or regions of the anti-C1q antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table A below under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Exemplary substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

In some embodiments, the substitutional variant involves substituting one or more hypervariable region residues of a parent antibody (e.g. a humanized or human anti-C1q antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a C1q protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-C1q antibody of the present disclosure) or antibody fragments.

(11) Other Antibody Modifications

Anti-C1q antibodies of the present disclosure, or antibody fragments thereof, can be further modified to contain additional non-proteinaceous moieties that are known in the art and readily available. In some embodiments, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

Nucleic Acids, Vectors, and Host Cells

Anti-C1q antibodies of the present disclosure may be produced using recombinant methods and compositions, e.g., as described in U.S. Pat. No. 4,816,567. In some embodiments, isolated nucleic acids having a nucleotide sequence encoding any of the anti-C1q antibodies of the present disclosure are provided. Such nucleic acids may encode an amino acid sequence containing the VL and/or an amino acid sequence containing the VH of the anti-C1q antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell).

Methods of making an anti-C1q antibody of the present disclosure are provided. In some embodiments, the method includes culturing a host cell of the present disclosure containing a nucleic acid encoding the anti-C1q antibody, under conditions suitable for expression of the antibody. In some embodiments, the antibody is subsequently recovered from the host cell (or host cell culture medium). See also Example 1.

For recombinant production of an anti-C1q antibody of the present disclosure, a nucleic acid encoding the anti-C1q antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-C1q antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-C1q antibody of the present disclosure.

Suitable host cells for cloning or expression of antibody-encoding vectors include prokaryotic or eukaryotic cells. For example, anti-C1q antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology, Vol.* 248 (B. K. C. Lo, ed., Humana Press, Totowa, N.J., 2003), pp. 245-254, describing expression of antibody fragments in *E. coli.*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology,* Vol. 248 (B. K. C. Lo, ed., Humana Press, Totowa, N.J.), pp. 255-268 (2003).

Pharmaceutical Compositions

Anti-C1q antibodies of the present disclosure can be incorporated into a variety of formulations for therapeutic use (e.g., by administration) or in the manufacture of a medicament (e.g., for treating or preventing a neurodegenerative disease or autoimmune disease) by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, Science 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-C1q antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-C1q antibody of the present disclosure may be used (e.g., administered to an individual in need of treatment with anti-C1q antibody, such as a human individual) in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-C1q antibodies of the present disclosure, normal dosage amounts may vary from about 10 ng/kg up to about 100 mg/kg of an individual's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An exemplary dosing regimen may include administering an initial dose of an anti-C1q antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-C1q antibody administered, can vary over time independently of the dose used.

Dosages for a particular anti-C1q antibody may be determined empirically in individuals who have been given one or more administrations of the anti-C1q antibody. Individuals are given incremental doses of an anti-C1q antibody. To assess efficacy of an anti-C1q antibody, any clinical symptom of a neurodegenerative disorder, inflammatory disorder, or autoimmune disorder can be monitored.

Administration of an anti-C1q antibody of the present disclosure can be continuous or intermittent, depending, for example, on the recipient's physiological condition, whether the purpose of the administration is therapeutic or prophylactic, and other factors known to skilled practitioners. The administration of an anti-C1q antibody may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

The present disclosure provides anti-C1q antibodies, and antigen-binding fragments thereof, which can bind to and neutralize a biologic activity of C1q. These anti-C1q antibodies are useful for preventing, reducing risk, or treating a range of diseases associated with complement activation, including, without limitation, neurodegenerative disorders, inflammatory disorders, and autoimmune disorders. Accordingly, as disclosed herein, anti-C1q antibodies of the present disclosure may be used for treating, preventing, or reducing risk of a disease associated with complement activation, including, without limitation, neurodegenerative disorders, inflammatory disorders, and autoimmune disorders, in an individual. In some embodiments, the individual has such a disease. In some embodiments, the individual is a human.

Neurodegenerative disorders that may be treated with anti-C1q antibodies of this disclosure include disorders associated with loss of nerve connections or synapses, including CF1-dependent synapse loss. Such disorders may include, without limitation, Alzheimer's disease, amyotrophic lateral sclerosis, multiple sclerosis, glaucoma, myotonic dystrophy, Down syndrome, Parkinson's disease, and Huntington's disease. In some neurodegenerative disorders, synapse loss is dependent on the complement receptor 3 (CR3)/C3 or complement receptor CR1. In some neurodegenerative disorders, synapse loss is associated with pathological activity-dependent synaptic pruning. In some disorders, synapses are phagocytosed by microglia. Accordingly, the anti-C1q antibodies of the present disclosure may be used to treat, prevent, or improve one or more symptoms of a neurodegenerative disorder of the present disclosure. In some embodiments, the present disclosure provides methods of treating, preventing, or improving one or more symptoms in individuals having a neurodegenerative disorder of the present disclosure by administering an anti-C1q antibody of the present disclosure to, for example, inhibit the interaction between C1q and an autoantibody, such as an anti-ganglioside autoantibody, the interaction of C1q and C1r, and/or the interaction of C1q and C1s.

Inflammatory or autoimmune diseases that may be treated with anti-C1q antibodies of this disclosure include, without limitation, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia. In some embodiments, autoimmune disease may further include, without limitation, Guillain-Barré syndrome, myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, polymyalgia rheumatica, temporal arteritis, and Wegener's granulomatosis.

In autoimmune diseases, such as Neuromyelitis Optica (NMO), autoantibodies activate the complement system. In NMO patients, the classical complement pathway is triggered by the binding of an autoantibody, such as an AQP4-targeted autoantibody, to its autoantigen, AQP4. AQP4 thereby activates the classical pathway of complement activation. In the first step of this activation process complement factor C1q binds to the autoantibody-autoantigen-immune complex. Autoantibodies may include naturally occurring antibodies, such as serum antibodies from NMO patients (commonly referred to as NMO-IgG) or monoclonal antibodies, such as rAb-53.

Accordingly, the anti-C1q antibodies of the present disclosure may be used to treat, prevent, or improve one or more symptoms of an inflammatory or autoimmune disease of the present disclosure. In some embodiments, the present disclosure provides methods of treating, preventing, or improving one or more symptoms in individuals having an inflammatory or autoimmune disease of the present disclosure by administering an anti-C1q antibody of the present disclosure to, for example, inhibit the interaction between C1q and an autoantibody, such as an anti-ganglioside autoantibody, the interaction of C1q and C1r, and/or the interaction of C1q and C1s.

Metabolic diseases that may be treated with anti-C1q antibodies include, without limitation, diabetes, such as type II diabetes, and obesity. In vitro and in vivo models of metabolic disorders that can be used for the testing of anti-C1q antibodies are well known in the art. Accordingly, the anti-C1q antibodies of the present disclosure may be used to treat, prevent, or improve one or more symptoms of a metabolic disease of the present disclosure. In some embodiments, the present disclosure provides methods of treating, preventing, or improving one or more symptoms in individuals having metabolic disease of the present disclosure by administering an anti-C1q antibody of the present disclosure to, for example, inhibit the interaction between C1q and an autoantibody, such as an anti-ganglioside autoantibody, the interaction of C1q and C1r, and/or the interaction of C1q and C1s.

Combination Treatments

The antibodies of the present disclosure may be used, without limitation, in combination with any additional treatment for neurodegenerative disorders, inflammatory disorders, and/or autoimmune disorders.

In some embodiments, an anti-C1q antibody of this disclosure is administered in therapeutically effective amounts in combination with a second anti-complement factor antibody (e.g., a neutralizing anti-complement factor antibody), such as an anti-C1s or anti-C1r antibody, or a second anti-C1q antibody. In some embodiments, an anti-C1q antibody of this disclosure is administered in therapeutically effective amounts with a second and a third neutralizing anti-complement factor antibody, such as a second anti-C1q antibody, an anti-C1s antibody, and/or an anti-C1r antibody.

In some embodiments, the anti-C1q antibodies of this disclosure are administered in combination with an inhibitor of antibody-dependent cellular cytotoxicity (ADCC). ADCC inhibitors may include, without limitation, soluble NK cell inhibitory receptors such as the killer cell Ig-like receptors (KIRs), which recognize HLA-A, HLA-B, or HLA-C and C-type lectin CD94/NKG2A heterodimers, which recognize HLA-E (see, e.g., López-Botet M., T. Bellón, M. Llano, F. Navarro, P. Garcia & M. de Miguel. (2000), Paired inhibitory and triggering NK cell receptors for HLA class I molecules. Hum. Immunol. 61: 7-17; Lanier L. L. (1998) Follow the leader: NK cell receptors for classical and nonclassical MHC class I. *Cell* 92: 705-707.), and cadmium (see, e.g., Immunopharmacology 1990; Volume 20, Pages 73-8).

In some embodiments, the antibodies of this disclosure are administered in combination with an inhibitor of the alternative pathway of complement activation. Such inhibitors may include, without limitation, factor B blocking antibodies, factor D blocking antibodies, soluble, membrane-bound, tagged or fusion-protein forms of CD59, DAF, CR1, CR2, Crry or Comstatin-like peptides that block the cleavage of C3, non-peptide C3aR antagonists such as SB 290157, Cobra venom factor or non-specific complement inhibitors such as nafamostat mesilate (FUTHAN; FUT-175), aprotinin, K-76 monocarboxylic acid (MX-1) and heparin (see, e.g., T. E. Mollnes & M. Kirschfink, Molecular Immunology 43 (2006) 107-121). In some embodiments, the antibodies of this disclosure are administered in combination with an inhibitor of the interaction between the autoantibody and its autoantigen.

Such inhibitors may include purified soluble forms of the autoantigen, or antigen mimetics such as peptide or RNA-derived mimotopes, including mimotopes of the AQP4 antigen. Alternatively, such inhibitors may include blocking agents that recognize the autoantigen and prevent binding of the autoantibody without triggering the classical complement pathway. Such blocking agents may include, e.g., autoantigen-binding RNA aptamers or antibodies lacking functional C1q binding sites in their Fc domains (e.g., Fab fragments or antibody otherwise engineered not to bind C1q).

Diagnostic Uses

The antibodies of this disclosure, or functional fragments thereof, also have diagnostic utility. This disclosure therefore provides for methods of using the antibodies of this disclosure, or functional fragments thereof, for diagnostic purposes, such as the detection of C1q in an individual or in tissue samples derived from an individual. In some embodiments, the individual is a human. In some embodiments, the individual is a human patient suffering from a neurodegenerative disorder or an inflammatory, or autoimmune disease. In some embodiments, the anti-C1q antibodies of this disclosure are used to detect synapses and synapse loss. For example, synapse loss may be measured in an individual suffering from a neurodegenerative disorder such as Alzheimer's disease or glaucoma.

In some embodiments, the diagnostic methods involve the steps of administering an anti-C1q antibody of this disclosure, or functional fragment thereof, to an individual and detecting the antibody bound to a synapse of the individual. Antibody-binding to synapses may be quantified, for example, by non-invasive techniques such as positron emission tomography (PET), X-ray computed tomography, single-photon emission computed tomography (SPECT), computed tomography (CT), and computed axial tomography (CAT).

In some embodiments, the diagnostic methods involve detecting synapses in a biological sample, such as a biopsy specimen, a tissue, or a cell. An anti-C1q antibody, or functional fragment thereof, is contacted with the biological sample and synapse-bound antibody is detected. The detection method may involve quantification of the synapse-bound antibody. Antibody detection in biological samples may occur with any method known in the art, including immunofluorescence microscopy, immunocytochemistry, immunohistochemistry, ELISA, FACS analysis or immunoprecipitation.

The quantification of synapse-bound antibodies provides a relative measure for the number of synapses present in the individual. Typically, synapses are quantified repeatedly over a period of time. The exact periodicity of synapse quantification depends on many factors, including the nature of the neurodegenerative disease, the stage of disease progression, treatment modalities and many other factors. Repeat measurements commonly reveal progressive synapse loss in individuals having a neurodegenerative disorder. Alternatively, relative synapse counts may be compared in populations of diseased individuals and healthy control individuals at a single time point. In diseased individuals undergoing treatment, the treatment's efficacy can be assessed by comparing the rates of synapse loss in the treated individuals with the rates of synapse loss in a control group. Control group members have received either no treatment or a control treatment, such as a placebo control.

Kits

The invention also provides kits containing an antibody of this disclosure, or a functional fragment thereof. Kits of the invention include one or more containers comprising a purified anti-C1q antibody of this disclosure. In some embodiments, the kits further include instructions for use in accordance with the methods of this disclosure. In some embodiments, these instructions comprise a description of administration of the anti-C1q antibody to treat or diagnose a disease associated with complement activation including, without limitation a neurodegenerative disorder (e.g., Alzheimer's disease), inflammatory disease, autoimmune disease, and/or metabolic disorder, according to any methods of this disclosure. In some embodiments, the instructions comprise a description of how to detect C1q, for example in an individual, in a tissue sample, or in a cell. The kit may further comprise a description of selecting an individual suitable for treatment based on identifying whether that individual has the disease and the stage of the disease.

The instructions generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a neurodegenerative disease. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an inhibitor of classical complement pathway. The container may further comprise a second pharmaceutically active agent.

Kits may optionally provide additional components such as buffers and interpretive information. Normally, the kit comprises a container and a label or package insert(s) on or associated with the container.

The invention will be more fully understood by reference to the following Examples. They should not, however, be construed as limiting the scope of the invention. All citations throughout the disclosure are hereby expressly incorporated by reference.

EXAMPLES

Example 1: Production of Anti-C1q Antibodies

The anti-C1q antibody M1 was generated by Antibody Solutions Inc. (Sunnyvale Calif.) by immunizing C1q knockout mice with human C1q using standard mouse immunization and hybridoma screening technologies (Milstein, C (1999). *Bioessays* 21: 966-73; Mark Page, Robin Thorpe, The Protein Protocols Handbook 2002 Editors: John M. Walker, pp 1111-1113).

The anti-C1q antibodies 1C7, 2A1, 3A2, and 5A3 were generated at ImmunoPrecise Ltd (Victoria, BC Canada) by immunizing mice with human C1q protein purified from human plasma (Complement Technology Inc. Tyler Texas, Cat #A-099). In brief, female BALB/c mice were injected intraperitoneal with 25 µg of protein in complete Freund's adjuvant (CFA) on Day 0 and boosts were done with 25 µg of C1q enzyme in incomplete Freund's adjuvant (IFA) on days 21, 42, 52, and a final intravenous boost on Day 63. Four days following the final boost the mice were euthanized, spleens removed and splenocytes were fused with the myeloma cell line SP2/0. Fused cells were grown on hypoxanthine-aminopterin-thymidine (HAT) selective semisolid media for 10-12 days and the resulting hybridomas clones were transferred to 96-well tissue culture plates and grown in HAT medium until the antibody titer was high. The antibody-rich supernatants of the clones were isolated and tested in an ELISA assay for reactivity with C1q. Positive clones were isotyped and cultured for 32 days (post HAT selection) to identify stable expressing clones.

A hybridoma cell line producing the anti-C1q antibody M1 and referred to as mouse hybridoma C1q-M1 7788-1(M) 051613 was deposited with ATCC on Jun. 6, 2013 having ATCC Accession Number PTA-120399. M1 was shown to bind specifically to human and mouse C1q and to neutralize biological functions of C1q, such as complement mediated hemolysis (see, e.g., Example 3).

Example 2: Anti-C1q Antibodies Specifically Bind to C1q

ELISA Screening

Anti-C1q antibodies 1C7, 2A1, 3A2, and 5A3 were screened for C1q-binding using standard ELISA protocols.

Briefly, the day before the assay was performed, 96-well microtiter plates were coated at 0.2 µg/well of C1q-enzyme antigen in 100 µL/well carbonate coating buffer pH 9.6 overnight at 4° C. Control wells were coated with human transferrin. Next, the plates were blocked with 3% milk powder in PBS for 1 hour at room temperature. Then, hybridoma tissue culture supernatants were plated at 100 µL/well for 1 hour at 37° C. with shaking. The secondary antibody (1:10,000 goat anti-mouse IgG/IgM(H+L)-HRP) was applied at 100 µL/well for 1.5 hours at room temperature with shaking. TMB substrate was added at 50 µL/well for 5 minutes at room temperature in the dark. The reaction was stopped with 50 µL/well 1M HCl and absorbance readings were taken at a wavelength of 450 nm.

Four hybridoma supernatants containing the anti-C1q antibodies 1C7, 2A1, 3A2, and 5A3 were tested for binding to human C1q (FIG. 1). By ELISA, all four supernatants showed strong binding signals in the presence of human C1q, whereas only background signals were observed in control wells containing human transferrin. This experiment demonstrated that the anti-C1q antibodies 1C7, 2A1, 3A2, and 5A3 specifically bind to human C1q.

Kinetic Analyses

The interactions of the full length anti-C1q antibody M1 with human and mouse C1q proteins were first measured in a kinetic mode and thermodynamic dissociation constants were subsequently calculated. Additionally, M1 binding data was compared with corresponding data obtained using the reference antibody 4A4B11. 4A4B11 is described in U.S. Pat. No. 4,595,654. The 4A4B11 producing hybridoma cell line is available from ATCC (ATCC HB-8327TM).

C1q-antibody interactions were measured using an OCTET™ System according to standard protocols and manufacturer's instructions. Briefly, human and mouse C1q proteins were immobilized separately on a biosensor at three concentrations (3 nM, 1.0 nM, and 0.33 nM). Next, the anti-C1q antibody M1 was injected onto the C1q-coated biosensor at a concentration of 2.0 µg/ml and the association constants ($k_{on}$) and dissociation constants ($k_{off}$) for anti-C1q antibodies M1 and 4A4B11 were measured. The data were fit by non-linear regression analysis and using the Octet Data Analysis software to yield affinity ($K_D$) and kinetic parameters ($k_{on/off}$) for the interactions of M1 and 4A4B11 with human and mouse C1q respectively (see Table B).

TABLE B

| Kinetic Analysis of M1 and 4A4B11 | | | | |
|---|---|---|---|---|
| Antibody | Antigen | $K_D$ (M) | $k_{on}$ (1/Ms) | $k_{off}$ (1/s) |
| M1 | human C1q | $1.28*10^{-11}$ | $5.18*10^6$ | $6.31*10^{-5}$ |
| M1 | mouse C1q | $3.23*10^{-11}$ | $1.81*10^6$ | $5.84*10^{-5}$ |
| 4A4B11 | human C1q | $2.29*10^{-11}$ | $4.49*10^6$ | $1.03*10^{-4}$ |
| 4A4B11 | mouse C1q | undetectable | undetectable | undetectable |

In this experimental series, anti-C1q antibody M1 was shown to bind both human and mouse C1q proteins with very high affinities ($K_D<10^{-10}$ M). By comparison, the reference antibody 4A4B11 was found to bind to human C1q, whereas binding to mouse C1q was undetectable. Whereas the affinities of M1 and 4A4B11 for human C1q were on the same order of magnitude (i.e., in the double-digit picomolar range; $K_D$~10-30 pM), the affinity of M1 for mouse C1q was determined to be about four orders of magnitude higher ($K_D$~30 pM) than that the affinity of 4A4B11 for mouse C1q ($K_D$~40 nM).

Anti-C1q Antibodies M1 and 4A4B11 do not Compete for C1q-Binding

Blocking experiments were performed to determine whether the anti-C1q antibodies M1 and 4A4B11 bind to the same or overlapping epitopes of human C1q or whether M1 and 4A4B11 bind to separate C1q epitopes.

To this end, M1 was coated on a biosensor chip (BIA-CORE™) and subsequently contacted with a combination of human C1q and M1, a combination of human C1q and 4A4B11, or human C1q alone. C1q-binding to M1 was followed for 10 min and dissociation of M1-C1q complexes was subsequently followed for 20 min. Relative binding signals were recorded at the end of the association and dissociation periods. Table C shows the results of these experiments.

TABLE C

Analysis of Simultaneous Interactions of M1 and 4A4B11 with human C1q

| Sensor Ab ID: | Antigen ID: | Solution Ab ID: | Association Response (nm) @ 600 s | DissociationResponse (nm) @ 1200 s |
|---|---|---|---|---|
| M1 | hC1q | M1 | −0.0119 | −0.00945 |
| M1 | hC1q | 4A4B11 | 0.8213 | 0.82139 |
| M1 | hC1q | None (Ag Only) | 0.4715 | 0.45137 |

It was found that C1q alone bound effectively to immobilized M1 antibody on the biosensor chip. Preincubation of C1q with soluble M1 antibody prevented all binding of the resulting M1-C1q complex to immobilized M1. By contrast, preincubation of C1q with 4A4B11 did not prevent the interaction of the resulting 4A4B11-C1q complex with immobilized M1. The larger relative binding signals observed in the binding experiment involving the 4A4B11-C1q complex relative to the binding experiment involving C1q alone is due to the fact that the relative binding signals correlate with the molecular weight of the soluble binding partners and that the 4A4B11-C1q complex has a higher molecular weight than C1q alone.

These results demonstrate that 4A4B11 does not compete with M1 for C1q binding. Therefore, 4A4B11 and M1 may recognize separate epitopes on C1q.

Example 3: Anti-C1q Antibodies Inhibit Complement-Mediated Hemolysis

Anti-C1q antibodies were tested in human and rodent hemolytic assays (CH50) for their ability to neutralize C1q and block its activation of the downstream complement cascade. CH50 assays were conducted essentially as described in *Current Protocols in Immunology* (1994) Supplement 9 Unit 13.1. In brief, 5 microliters (μl) of human serum (Cedarlane, Burlington, N.C.), 0.625 μl of Wistar rat serum, or 2.5 μl of C57Bl/6 mouse serum was diluted to 50 μl of GVB buffer (Cedarlane, Burlington, N.C.) and added to 50 μl of the monoclonal antibodies (1 μg) diluted in GVB buffer. The antibody:serum mixture was pre-incubated for 30 minutes on ice and then added to 100 μl of EA cells ($2 \times 10^8$/ml) for rat and human assays, and $4 \times 10^7$/ml for mouse assays. The EA cells were generated exactly as specified in Current Protocols using Sheeps blood in Alsever's (Cedarlane Cat #CL2581) and hemolysin (Cedalane Cat #CL9000). The EA cells, serum and antibody mixture was incubated for 30 minutes at 37° C. and then placed on ice. Next 1.2 ml of 0.15 M NaCl was added to the mixture and the $OD_{412}$ of the sample was read in a spectrophotometer to determine the amount of cell lysis. The percent inhibition of the test antibodies was determined relative to a control mouse IgG1 antibody (Abcam ab18447).

A modified CH50 assay (also referred to as C1F hemolysis assay) was performed that provided limiting quantities of the C1 complex from human serum to provide greater sensitivity for assessing C1 activity and potential C1 inhibition. In brief, the assay was conducted as follows. First, $3 \times 10^7$ sheep red blood cells (RBC) were incubated with anti-sheep RBC IgM antibody to generate activated erythrocytes (EA cells). The EA cells were then incubated with purified C4b protein to create EAC4b cells. EAC4b cells were subsequently incubated with diluted (1:1000-1:10000) normal human serum (NHS) that was pre-incubated with or without anti-C1q and control mouse IgG antibodies, to provide a limiting quantity of human C1. Next, the resulting EAC14 cells were incubated with purified human C2 protein to generate EAC14b2a cells. Finally, guinea pig serum was added in an EDTA buffer and incubated at 37° C. for 30 minutes. Cell lysis was measured in a spectrophotometer at a wavelength of 450 nm.

Figure 2:
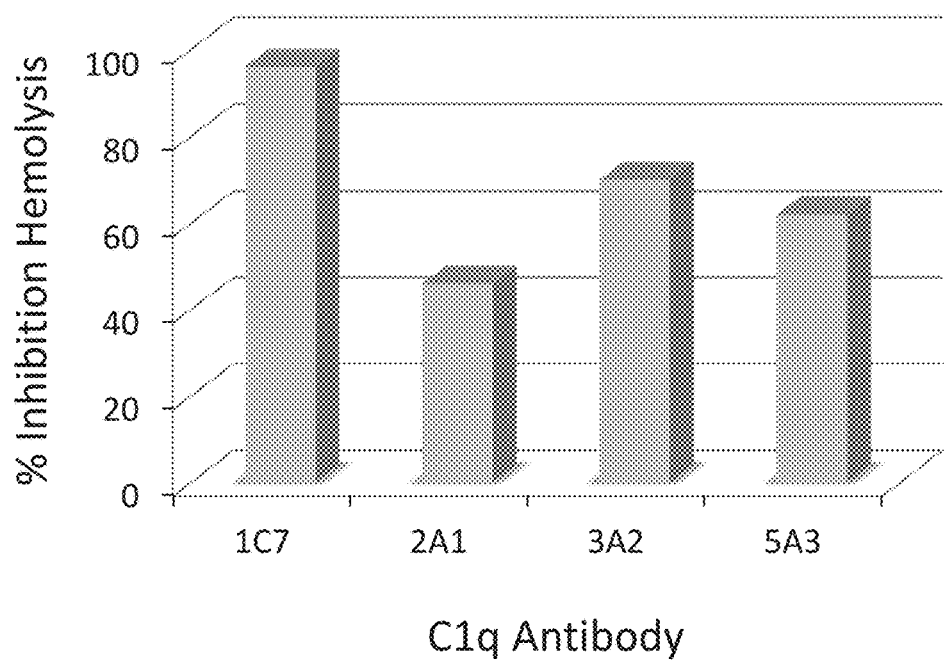
FIG. 2 illustrates the C1q-neutralizing activities of anti-C1q antibodies 1C7, 2A1, 3A2, and 5A3 in a human CH50 hemolytic assay in a single-dose format.

First, four C1q-binding antibodies (1C7, 2A1, 3A2, and 5A3) were tested in the human CH50 assay at a single concentration (1 μg) (FIG. 2). All four antibodies were found to inhibit hemolysis. The anti-C1q antibody 1C7 inhibited hemolysis at greater than 90%, 2A1 inhibited hemolysis at greater than 40%, 3A2 inhibited hemolysis at greater than 60%, and 5A3 inhibited hemolysis at greater than 50%.

Figure 3:
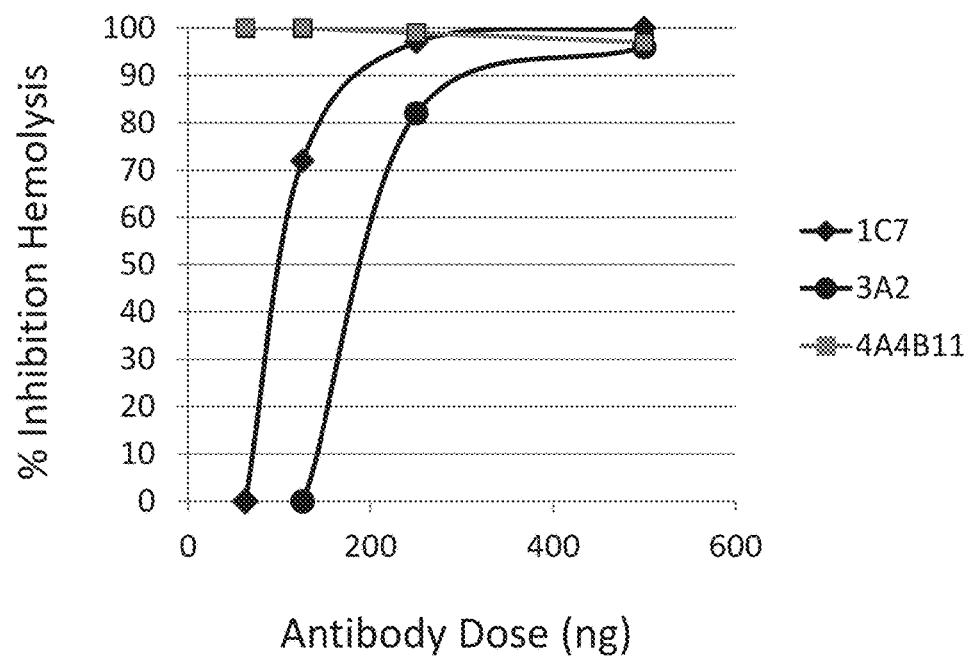
FIG. 3 illustrates the C1q-neutralizing activities of anti-C1q antibodies 1C7, 3A2, and 4A4B11 in a human CH50 hemolytic assay in a dose-response format.

Next, anti-C1q antibodies 1C7 and 3A2 were tested in the human CH50 hemolysis assay in a dose-response format (FIG. 3). Anti-C1q antibody 4A4B11 was used as a reference. Both 1C7 and 3A2 antibodies inhibited CH50 hemolysis in a dose-dependent manner. Approximately 100 ng of the 1C7 antibody and approximately 200 ng of the 3A2 were required to inhibit 50% of the hemolysis observed (FIG. 3).

Figure 4A:
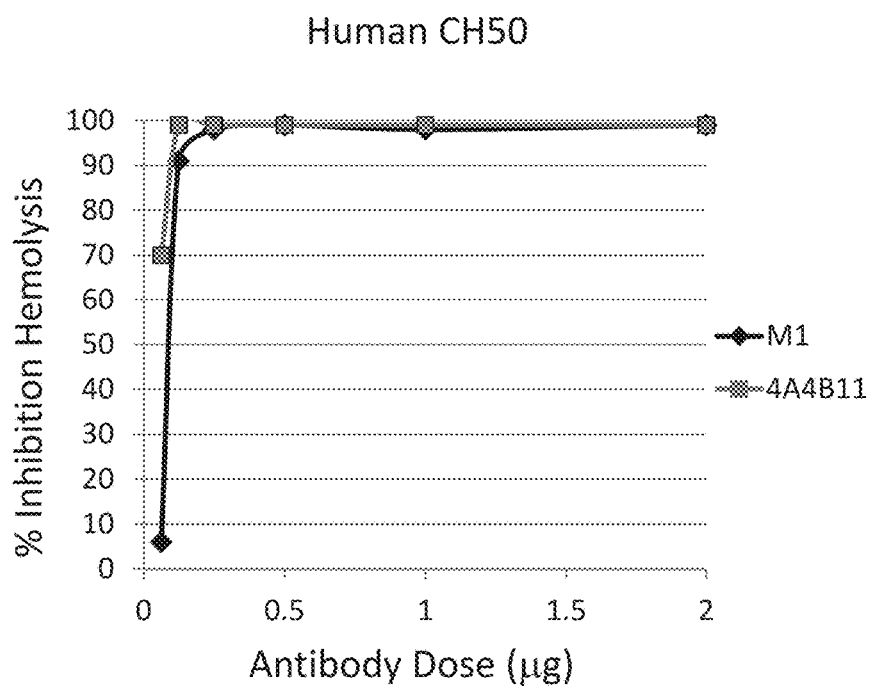
FIG. 4A, FIG. 4B, and FIG. 4C illustrate the C1q-neutralizing activities of anti-C1q antibodies M1 and 4A4B11 in human, mouse, and rat CH50 hemolytic assays in a dose-response format.
Figure 4B:
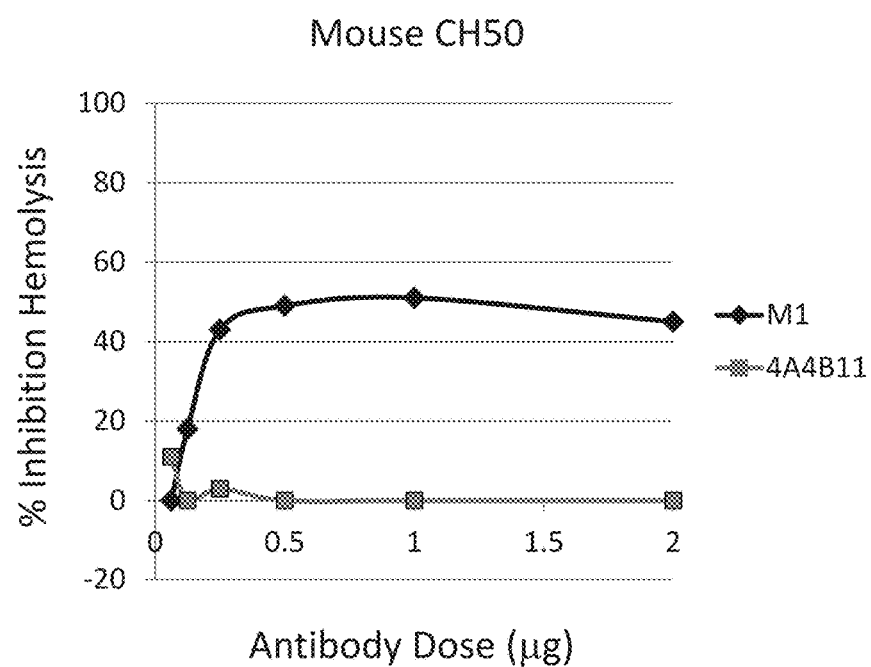
Figure 4C:
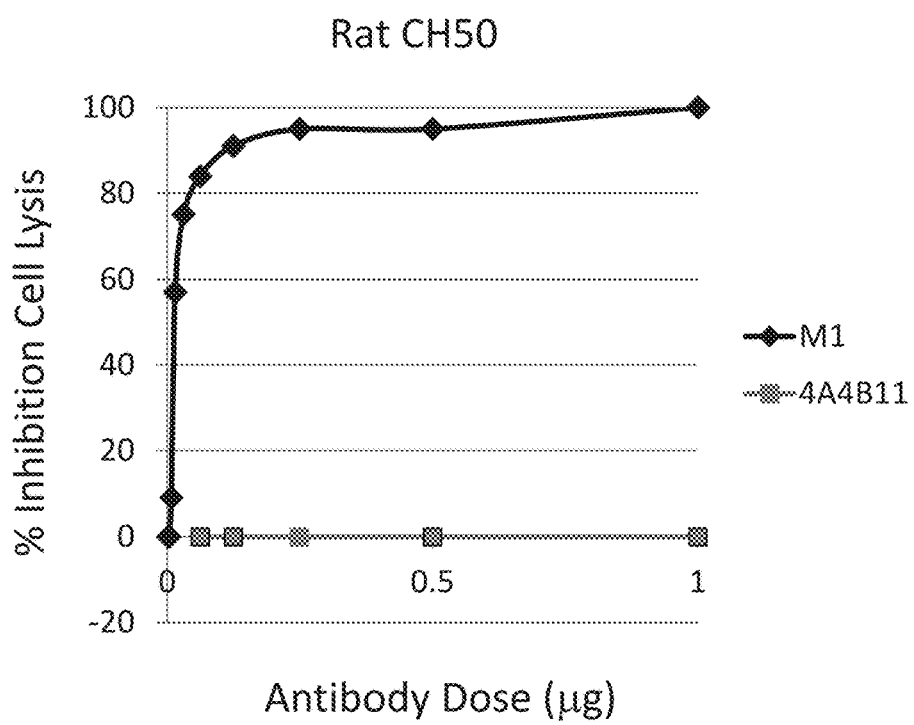

Anti-C1q antibody M1 was tested for its C1q neutralizing activity in human, mouse, and rat CH50 assays (FIG. 4A-C). Testing was conducted in dose-response formats. Anti-C1q antibody 4A4B11 was used as a reference. M1 was demonstrated to neutralize C1q activity in human, mouse, and rat CH50 hemolysis assays in a dose-dependent manner (FIG. 4A-4C). By contrast, 4A4B11 was found to neutralize C1q activity only in the human CH50 assay, whereas the reference antibody was inactive in the mouse and rat CH50 hemolysis assays (up to 2 μg). In the human and rat CH50 hemolysis assays M1 inhibited greater than 90% and up to 100% of hemolysis (FIGS. 4A and 4C); in the mouse assay M1 inhibited greater than 50% of hemolysis (FIG. 4B). In the human CH50 assay, less than 125 ng of M1 were required to achieve 50% inhibition of hemolysis. In the mouse CH50 assay, approximately 500 ng of M1 were required to achieve 50% inhibition of hemolysis. In the rat CH50 assay, less than 16 ng were required to achieve 50% inhibition of hemolysis.

Example 4: Epitope Mapping for Antibody 4A4B11 and M1

In order to determine the nature of the epitope (i.e., linear or conformational), the inhibition of the interaction between the C1Q protein and the antibodies 4A4B11 (ANN-001) and M1 (ANN-005) by unstructured peptides generated by proteolysis of the C1q antigen was evaluated. If the peptides generated by complete proteolysis of the antigen are able to inhibit the binding of the antigen on the antibody, the interaction is not based on conformation, and the epitope is linear. If the peptides generated by complete proteolysis of the antigen are unable to inhibit the binding of the antigen on the antibodies 4A4B11 and M1, the conformation is necessary for interaction. Based on the data described in detail below, unstructured peptides generated by digestion of native C1q did not compete with intact C1q for binding to the 4A4B11 (ANN-001) and M1 (ANN-005) antibodies (see FIG. 2), suggesting that the C1q epitope for these antibodies is a complex conformational epitope.

In order to determine the key residues of the conformational C1q epitope that binds of ANN-001 and ANN-005 on C1Q antigen with high resolution the antibody/antigen complexes were incubated with deuterated cross-linkers and subjected to multi-enzymatic proteolytic cleavage. After enrichment of the cross-linked peptides, the samples were analyzed by high resolution mass spectrometry (nLC-Orbitrap MS) and the data generated analyzed using XQuest software. The analysis described below indicates that antibibody 4A4B11 (ANN-001) binds to an epitope that includes amino acids S202 and K219 of human C1QA and Y225 of human C1QC, and antibody M1 (ANN-005) binds to an epitope that includes amino acid K219 of human C1QA and S185 of human C1QC. See the amino acid sequence alignment of human and mouse C1qA and C1qC as shown below.

Amino Acid Sequence Alignment of Human and Mouse C1qA

```
MEGPRGWLVLCVLAISLASMVTEDLCRAPDGKKGEAGRPGRRGRPGLKGEQGEPGAPGIR human
METSQGWLVACVLTMTLVWTVAEDVCRAPNGKDGAPGNPGRPGRPGLKGERGEPGAAGIR mouse
**  .:****  ***.::.*.   *.**:****:**.*  .*.*** ********:***** .***

TGIQGLKGDQGEPGPSGNPGKVGYPGPSGPLGARGIPGIKGTKGSPGNIKDQPRPAFSAI human
TGIRGFKGDPGESGPPGKPGNVGLPGPSGPLGDSGPQGLKGVKGNPGNIRDQPRPAFSAI mouse
***:*:***.**.**.*.**:** ********   *  *:**.**.****:**********

RRNPPMGGNVVIFDTVITNQEEPYQNHSGRFVCTVPGYYYFTFQVLSQWEICLSIVSSSR human
RQNPMTLGNVVIFDKVLTNQESPYQNHTGRFICAVPGFYYFNFQVISKWDLCLFIKSSSG mouse
*:**   *******.*:****:*****.***:*.***:***.***:*:*::** * ***

GQVRRSLGFCDTTNKGLFQVVSGGMVLQLQQGDQVWVEKDPKKGHIYQGSEADSVFSGFL human
GQPRDSLSFSNTNNKGLFQVLAGGTVLQLRRGDEVWIEKDPAKGRIYQGTEADSIFSGFL mouse
** *.**.*.:*.********:.** ****.:** **:****  ** :****.****:*****

IFPSA human (SEQ ID NO: 1)
IFPSA mouse (SEQ ID NO: 14)
*****
```

Amino Acid Sequence Alignment of Human and Mouse C1qC

```
MDVGPSSLPHLGLKLLLLLLLLP-LRGQANTGCYGIPGMPGLPGAPGKDGYDGLPGPKGE human
MVVGPSCQPPCGLCLLLLFLLALPLRSQASAGCYGIPGMPGMPGAPGKDGHDGLQGPKGE mouse
*.****. ** ** ****.**    **.**.:**********:********:***.*****

PGIPAIPGIRGPKGQKGEPGLPGHPGKNGPMGPPGMPGVPGPMGIPGEPGEEGRYKQKFQ human
PGIPAVPGTRGPKGQKGEPGMPGHRGKNGPRGTSGLPGDPGPRGPPGEPGVEGRYKQKHQ mouse
*****:** ***********:***:*****.*..*:*** *** *.*****.*******:*

SVFTVTRQTHQPPAPNSLIRFNAVLTNPQGDYDTSTGKFTCKVPGLYYFVYHASHTANLC human
SVFTVTRQTTQYPEANALVRFNSVVTNPQGHYNPSTGKFTCEVPGLYYFVYYTSHTANLC mouse
*********  *  . *:*:***:*.****** *:*******:*********::*******

VLLYRSGVKVVTFCGHTSKTNQVNSGGVLLRLQVGEEVWLAVNDYYDMVGIQGSDSVFSG human
VHLNLNLARVASFCDHMFNSKQVSSGGVLLRLQRGDEVWLSVNDYNGMVGIEGSNSVFSG mouse
* *  .  ..:*.**.*   :::**.*********  *:****  **.****:****:*****

FLLFPD human (SEQ ID NO: 3)
FLLFPD mouse (SEQ ID NO: 15)
******
```

1. Identification of the C1q/Antibody Complexes by Mass Spectrometry

The C1q/antibody complexes were generated by mixing equimolar solutions of C1q antigen and antibody (4 µM in 5 µl each). One µl of the mixture obtained was mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample was spotted on the MALDI plate (SCOUT 384). After crystallization at room temperature, the plate was introduced in the MALDI mass spectrometer and analysed immediately. The analysis has been repeated in triplicate. FIG. 5A and FIG. 5B show the presence of the antigen, antibody and antigen/antibody complexes for C1q/4A4B11 (FIG. 5A) and C1q/M1 (FIG. 5B). Peaks are present at the predicted molecular weights of monomeric antibody (~150 kDa) and C1q monomer (~460 kDa) and there is a 1:1 complex of antibody:antigen present at ~615 kDa.

2. Unstructured C1q Peptides Generated by Proteolysis do not Compete for Binding of C1q to Antibody To determine if the C1q/antibody complexes could be competed with peptides the C1q antigen was digested with immobilized pepsin. 25 µl of the antigen with a concentration of 10 µM were mixed with immobilized pepsin 5 µM and incubate at room temperature for 30 minutes. After the incubation time the sample was centrifuged and the supernatant was pipetted. The completion of the proteolysis was controlled by High-Mass MALDI mass spectrometry in linear mode. The pepsin proteolysis was optimized in order to obtain a large amount of peptide in the 1000-3500 Da range. Next, 5 µl of the antigen peptides generated by proteolysis were mixed with 5 µl of ANN-001 or ANN-005 (8 µM) and incubated at 37° C. for 6 hours. After incubation of ANN-001 or ANN-005 with the C1Q antigen peptides, 5 µl of the mixture was mixed with 5 µl of the C1Q antigen (4 µM) so the final mix contained 2 µM/2 µM/2.5 µM of C1Q antigen/4A4B11 or M1/C1Q antigen Peptides.

The MALDI ToF MS analysis was performed using CovalX's HM3 interaction module with a standard nitrogen laser and focusing on different mass ranges from 0 to 2000 kDa. For the analysis, the following parameters have been applied for Mass Spectrometer: Linear and Positive mode; Ion Source 1: 20 kV; Ion Source 2: 17 kV; Pulse Ion Extraction: 400 ns; for HM3: Gain Voltage: 3.14 kV; Gain Voltage: 3.14 kV; Acceleration Voltage: 20 kV.

To calibrate the instrument, an external calibration with clusters of Insulin, BSA and IgG has been applied. For each sample, 3 spots were analyzed (300 laser shots per spots). The presented spectrum corresponds to the sum of 300 laser shots. The MS data were analyzed using the Complex Tracker analysis software version 2.0 (CovalX Inc).

Figure 6A:
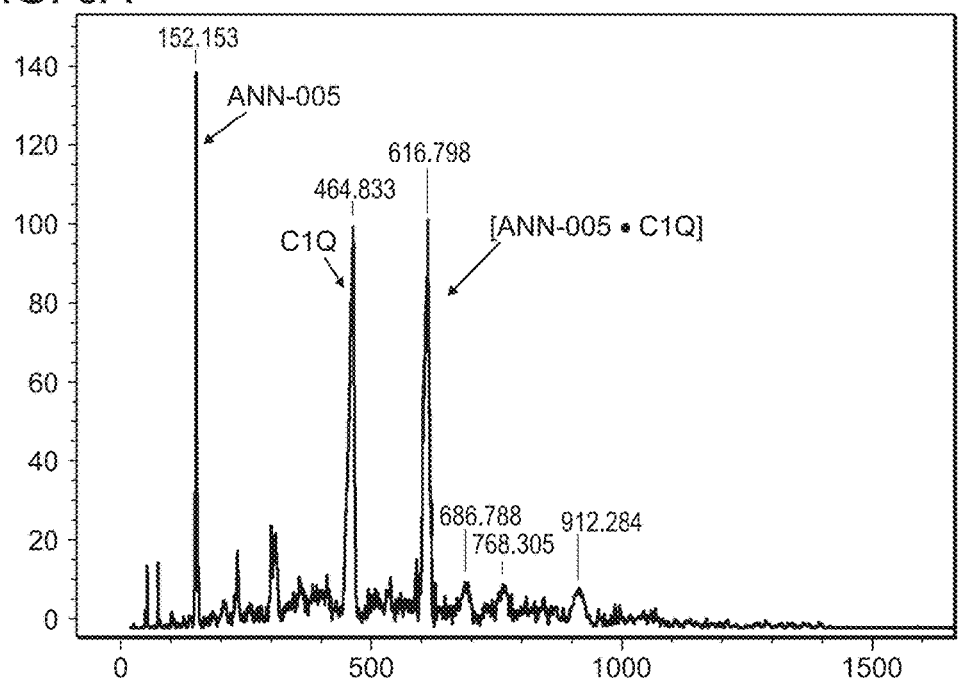
FIG. 6A and FIG. 6B illustrate C1q peptides do not compete with intact C1q for binding to monoclonal antibody ANN-005 (M1).
Figure 6B:
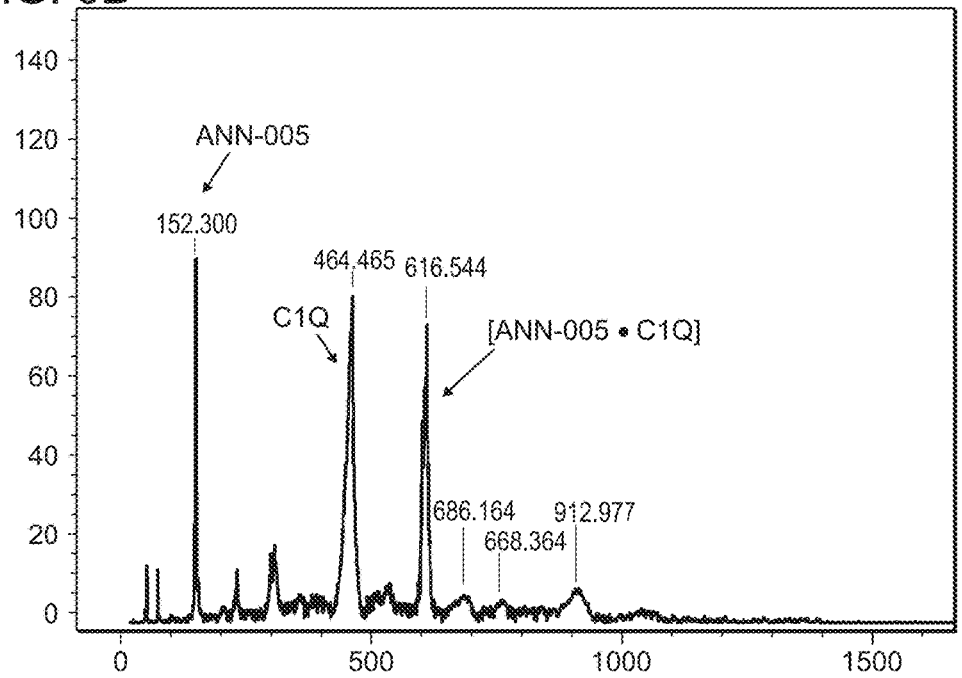

The results are shown in FIG. 6A and FIG. 6B, and demonstrate that C1q peptides do not compete with intact C1q for binding to monoclonal antibody ANN-005 (M1).

3. Identification of the Conformational Epitopes for C1q Binding to ANN-001 and ANN-005

Using chemical cross-linking, High-Mass MALDI mass spectrometry and nLC-Orbitrap mass spectrometry the interaction interface between the antigen C1Q and two monoclonal antibodies ANN-001 and ANN-005 was characterized. 5 µl of the sample C1Q antigen (concentration 4 µM) was mixed with 5 µl of the sample ANN-001 (Concentration 4 µM) or ANN-005 (Concentration 4 µM) in order to obtain an antibody/antigen mix with final concentration 2 µM/2 µM. The mixture was incubated at 37° C. for 180 minutes. In a first step, 1 mg of DiSuccinimidylSuberate H12 (DSS-H12) cross-linker was mixed with 1 mg of DiSuccinimidyl-Suberate D12 (DSS-D12) cross-linker. The 2 mg prepared were mixed with 1 ml of DMF in order to obtain a 2 mg/ml solution of DSS H12/D12. 10 µl of the antibody/antigen mix prepared previously were mixed with 1 µl of the solution of cross-linker d0/d12 prepared (2 mg/ml). The solution was incubated 180 minutes at room temperature in order to achieve the cross-linking reaction. In order to facilitate the proteolysis, it was necessary to reduce the disulfide bound present in this protein. The cross-linked sample was mixed with 20 µl of ammonium bicarbonate (25 mM, pH 8.3). After mixing 2.5 µl of DTT (500 mM) is added to the solution. The mixture was then incubated 1 hour at 55° C. After incubation, 2.5 µl of iodioacetamide (1 M) was added before 1 hour of incubation at room temperature in a dark room. After incubation, the solution was diluted 1/5 by adding 120 µl of the buffer used for the proteolysis. 145 µl of the reduced/alkyled cross-linked sample was mixed with 2 µl of trypsin (Sigma, T6567). The proteolytic mixture was incubated overnight at 37° C. For a-chymotrypsin proteolysis, the buffer of proteolysis was Tris-HCL 100 mM, CaCl$_2$ 10 mM, pH7.8. The 145 µl of the reduced/alkyled cross-linked complex was mixed with 2 µl of α-chymotrypsin 200 µM and incubated overnight at 30° C. For this analysis, an nLC in combination with Orbitrap mass spectrometry were used. The cross-linker peptides were analyzed using Xquest version 2.0 and stavrox software. The peptides identified and cross-linked amino acids are indicated in Table D below.

TABLE D

C1q cross-linked peptides and contact residues necessary for ANN-001 and ANN-005 binding

| Protease Digest | X-linked Peptide | C1q Subunit | Contact Residue | Antibody |
| --- | --- | --- | --- | --- |
| Trypsin | GLFQVVSGGMVLQLQQGDQVWVEK (SEQ ID NO: 25, residues 196-219 of SEQ ID NO: 1) | C1qA | K219 | ANN-001 |
| Trypsin | FQVVSGGMVLQL (SEQ ID NO: 26, residues 198-209 of SEQ ID NO: 1) | C1qA | S202 | ANN-001 |
| Chymotrypsin | YDMVGIQGSDSVFSGF (SEQ ID NO: 21, residues 225-240 of SEQ ID NO: 3) | C1qC | Y225 | ANN-001 |
| Trypsin | GLFQVVSGGMVLQLQQGDQVWVEK (SEQ ID NO: 25, residues 196-219 of SEQ ID NO: 1) | C1qA | K219 | ANN-005 |

TABLE D-continued

C1q cross-linked peptides and contact residues necessary for ANN-001 and ANN-005 binding

| Protease Digest | X-linked Peptide | C1q Subunit | Contact Residue | Antibody |
|---|---|---|---|---|
| Chymotrypsin | RSGVKVVTF (SEQ ID NO: 24, residues 184-192 of SEQ ID NO: 3) | C1qC | S185 | ANN-005 |

4. Light Chain and Heavy Chain Variable Domain Sequences of Antibody M1

Using standard techniques, the nucleic acid and amino acid sequences encoding the light chain variable and the heavy chain variable domain of antibody M1 were determined. T he amino acid sequence of the light chain variable domain of antibody M1 is: DVQITQSPSYLAASPGETITINCRASKSINKYLAWYQEKPGKTNKLLIYSGSTLQSGIPSR FSGSGSGTDFTLTISSLEPEDFAMYYCQQHNEYPLTFGAGTKLELK (SEQ ID NO:4). The hyper variable regions (HVRs) of the light chain variable domain are depicted in bolded and underlined text. In some embodiments, the HVR-L1 of the M1 light chain variable domain has the sequence RASKSINKYLA (SEQ ID NO:5), the HVR-L2 of the M1 light chain variable domain has the sequence SGSTLQS (SEQ ID NO:6), and the HVR-L3 of the M1 light chain variable domain has the sequence QQHNEYPLT (SEQ ID NO:7).

The amino acid sequence of the heavy chain variable domain of antibody M1 is: QVQLQQPGAELVKPGASVKLSCKSSGYHFTSYWMHWVKQRPGQGLEWIGVIHPNSGSINYNEKFESKATLTVDKSSSTAYMQLSSLTSEDSAVYYCAGERDSTEVLPMDYWGQG TSVTVSS (SEQ ID NO:8). The hyper variable regions (HVRs) of the heavy chain variable domain are depicted in bolded and underlined text. In some embodiments, the HVR-H1 of the M1 heavy chain variable domain has the sequence GYHFTSYWMH (SEQ ID NO:9), the HVR-H2 of the M1 heavy chain variable domain has the sequence VIHPNSGSINYNEKFES (SEQ ID NO:10), and the HVR-H3 of the M1 heavy chain variable domain has the sequence ERDSTEVLPMDY (SEQ ID NO:11).

The nucleic acid sequence encoding the light chain variable domain was determined to be:

```
                                          (SEQ ID NO: 12)
GATGTCCAGATAACCCAGTCTCCATCTTATCTTGCTGCATCTCCTGGAGAA

ACCATTACTATTAATTGCAGGGCAAGTAAGAGCATTAACAAATATTTAGCC

TGGTATCAAGAGAAACCTGGGAAAACTAATAAGCTTCTTATCTACTCTGGA

TCCACTTTGCAATCTGGAATTCCATCAAGGTTCAGTGGCAGTGGATCTGGT

ACAGATTTCACTCTCACCATCAGTAGCCTGGAGCCTGAAGATTTTGCAATG

TATTACTGTCAACAACATAATGAATACCCGCTCACGTTCGGTGCTGGGACC

AAGCTGGAGCTGAAA.
```

The nucleic acid sequence encoding the heavy chain variable domain was determined to be:

```
                                          (SEQ ID NO: 13)
CAGGTCCAACTGCAGCAGCCTGGGGCTGAGCTGGTAAAGCCTGGGGCTTCA

GTGAAGTTGTCCTGCAAGTCTTCTGGCTACCATTTCACCAGCTACTGGATG

CACTGGGTGAAGCAGAGGCCTGGACAAGGCCTTGAGTGGATTGGAGTGATT

CATCCTAATAGTGGTAGTATTAACTACAATGAGAAGTTCGAGAGCAAGGCC

ACACTGACTGTAGACAAATCCTCCAGCACAGCCTACATGCAACTCAGCAGC

CTGACATCTGAGGACTCGGCGGTCTATTATTGTGCAGGAGAGAGAGATTCT

ACGGAGGTTCTCCCTATGGACTACTGGGGTCAAGGAACCTCAGTCACCGTC

TCCTCA.
```

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Deposit of Material

The following materials have been deposited according to the Budapest Treaty in the American Type Culture Collection, ATCC Patent Depository, 10801 University Blvd., Manassas, Va. 20110-2209, USA (ATCC):

| Sample ID | Isotype | Deposit Date | ATCC Accession No. |
|---|---|---|---|
| Mouse hybridoma C1qM1 7788-1(M) 051613 producing anti-C1q antibody M1 | IgG1, kappa | Jun. 6, 2013 | PTA-120399 |

The hybridoma cell line producing the M1 antibody (mouse hybridoma C1qM1 7788-1(M) 051613) has been deposited with ATCC under conditions that assure that access to the culture will be available during pendency of the patent application and for a period of 30 years, or 5 years after the most recent request, or for the effective life of the patent, whichever is longer. A deposit will be replaced if the deposit becomes nonviable during that period. The deposit is available as required by foreign patent laws in countries wherein counterparts of the subject application, or its progeny are filed. However, it should be understood that the availability of the deposit does not constitute a license to practice the subject invention in derogation of patent rights granted by governmental action.

What is claimed is:

1. A method of treating a disease associated with C1q mediated activation of the classical complement pathway, the method comprising administering a therapeutically effective dose of an anti-C1q antibody, comprising (a) a light chain variable domain and a heavy chain variable domain, wherein the light chain variable domain comprises the hypervariable region (HVR)-L1, HVR-L2, and HVR-L3 of the monoclonal antibody M1 produced by a hybridoma cell line with ATCC Accession Number PTA-120399; and wherein the heavy chain variable domain comprises the HVR-H1, HVR-H2, and HVR-H3 of the monoclonal antibody M1 produced by a hybridoma cell line with ATCC Accession Number PTA-120399; or (b) a heavy chain HVR selected from HVR-H1 comprising the amino acid sequence of SEQ ID NO: 9, HVR-H2 comprising the amino acid sequence of SEQ ID NO: 10, and HVR-H3 comprising the amino acid sequence of SEQ ID NO: 11.

2. The method of claim 1, wherein the disease associated with C1q mediated activation of the classical complement pathway is a neurodegenerative disorder.

3. The method of claim 2, wherein the neurodegenerative disorder is associated with loss of synapses or loss nerve connections.

4. The method of claim 2, wherein the neurodegenerative disorder is associated with synapse loss that is dependent on complement receptor 3 (CR3) or complement receptor CR1.

5. The method of claim 2, wherein the neurodegenerative disorder is associated with pathological activity-dependent synaptic pruning.

6. The method of claim 2, wherein the neurodegenerative disorder is associated with synapse phagocytosis by microglia.

7. The method of claim 2, wherein the neurodegenerative disorder is Alzheimer's disease, amyotrophic lateral sclerosis, multiple sclerosis, glaucoma, myotonic dystrophy, Down syndrome, Parkinson's disease, or Huntington's disease.

8. The method of claim 1, wherein the disease associated with C1q mediated activation of the classical complement pathway is an inflammatory disease, autoimmune disease, or metabolic disorder.

9. The method of claim 8, wherein the inflammatory disease, autoimmune disease, or metabolic disorder is diabetes, obesity, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases, age-related macular degeneration (AMD), choroidal neovascularization (CNV), uveitis, diabetic retinopathy, ischemia-related retinopathy, endophthalmitis, intraocular neovascular disease, diabetic macular edema, pathological myopia, von Hippel-Lindau disease, histoplasmosis of the eye, Neuromyelitis Optica (NMO), Central Retinal Vein Occlusion (CRVO), corneal neovascularization, retinal neovascularization, allo-transplantation, hyperacute rejection, hemodialysis, chronic occlusive pulmonary distress syndrome (COPD), asthma, or aspiration pneumonia.

10. The method of claim 1, wherein the disease associated with C1q mediated activation of the classical complement pathway is myasthenia gravis, Diabetes mellitus type 1, Hashimoto's thyroiditis, Addison's disease, Coeliac disease, Crohn's disease, pernicious anaemia, Pemphigus vulgaris, vitiligo, autoimmune hemolytic anemias, paraneoplastic syndromes, a vasculitis disease, polymyalgia rheumatica, temporal arteritis, or Wegener's granulomatosis.

11. The method of claim 1, wherein the antibody comprises a light chain variable domain comprising the amino acid sequence of SEQ ID NO:4.

12. The method of claim 1, wherein the antibody comprises a heavy chain variable domain comprising the amino acid sequence of SEQ ID NO:8.

13. The method of claim 1, wherein the antibody binds specifically to human C1q, mouse C1q, and rat C1q.

14. The method of claim 1, wherein the antibody has a dissociation constant ($K_D$) for human C1q and mouse C1q less than about 30 nM.

15. The method of claim 1, wherein the antibody specifically binds to C1q and inhibits CH50 hemolysis.

16. The method of claim 15, wherein CH50 hemolysis comprises human, mouse, or rat CH50 hemolysis.

17. The method of claim 15, wherein the antibody is capable of neutralizing at least 50%, at least 80%, or at least 90% of CH50 hemolysis.

18. The method of claim 15, wherein the antibody is capable of neutralizing at least 50% of CH50 hemolysis at a dose of less than 200 ng/ml, less than 100 ng/ml, less than 50 ng/ml, or less than 20 ng/ml.

19. The method of claim 1, wherein the antibody is a murine, humanized, or chimeric antibody.

20. The method of claim 11, wherein the antibody comprises a heavy chain variable domain comprising the amino acid sequence of SEQ ID NO:8.

21. The method of claim 11, wherein the antibody has a dissociation constant ($K_D$) for human C1q and mouse C1q less than about 30 nM.

22. The method of claim 12, wherein the antibody has a dissociation constant ($K_D$) for human C1q and mouse C1q less than about 30 nM.

23. The method of claim 11, wherein the antibody is an antibody fragment, wherein the antibody fragment is a Fab, F(ab')$_2$ or Fab' fragment.

24. The method of claim 12, wherein the antibody is an antibody fragment, wherein the antibody fragment is a Fab, F(ab')$_2$ or Fab' fragment.

25. The method of claim 20, wherein the antibody is an antibody fragment, wherein the antibody fragment is a Fab, F(ab')$_2$ or Fab' fragment.

26. The method of claim 1, wherein the antibody is of the IgG class.

27. The method of claim 26, wherein the antibody has an IgG1, IgG2, IgG3, or IgG4 isotype.

28. The method of claim 1, wherein the antibody specifically binds to and neutralizes a biological activity of C1q.

29. The method of claim 28, wherein the biological activity is (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to beta-amyloid, or (10) C1q binding to calreticulin.

30. The method of claim 28, wherein the biological activity is (1) activation of the classical complement activation pathway, (2) activation of antibody and complement dependent cytotoxicity, (3) CH50 hemolysis, (4) synapse loss, (5) B-cell antibody production, (6) dendritic cell maturation, (7) T-cell proliferation, (8) cytokine production (9) microglia activation, (10) Arthus reaction, (11) phagocytosis of synapses or nerve endings, or (12) activation of complement receptor 3 (CR3/C3) expressing cells.

* * * * *